(12) United States Patent
Cockrum

(10) Patent No.: US 6,770,301 B2
(45) Date of Patent: Aug. 3, 2004

(54) COMPOSITION AND METHOD FOR MODULATING IMMUNE RESPONSIVENESS

(75) Inventor: Richard Cockrum, Perry, IA (US)

(73) Assignee: Immuno-Dynamics, Inc., Perry, IA (US)

( * ) Notice: Subject to any disclaimer, the term of this patent is extended or adjusted under 35 U.S.C. 154(b) by 0 days.

(21) Appl. No.: 10/128,326

(22) Filed: Apr. 23, 2002

(65) Prior Publication Data

US 2003/0198688 A1 Oct. 23, 2003

(51) Int. Cl.⁷ .............................................. A61K 35/20
(52) U.S. Cl. ....................................................... 424/535
(58) Field of Search ......................................... 424/535

(56) References Cited

U.S. PATENT DOCUMENTS 5,846,569 A * 12/1998 Anderson et al.

* cited by examiner

Primary Examiner—Leon B. Lankford, Jr.
Assistant Examiner—Susan D. Coe
(74) Attorney, Agent, or Firm—Daniel A. Rosenberg; Kent A. Herink; Davis, Brown, Koehn, Shors & Roberts, P.C.

(57) ABSTRACT

The invention is a composition and method for non-specific enhancement of immune responses in human and animal recipients. A colostrum-derived feed additive (CDFA) for human or veterinary use comprises a sprayed-dried preparation of pasteurized and homogenized first milking colostrum that enhances immune responses in a recipient receiving an oral administration. Generally, CDFA is administered in a conditioning dose once per day during a conditioning period of time from about 7 to 14 days, and then in a maintenance dose administered once per day during a period that follows the conditioning period. The maintenance dose is about one-half the concentration of the conditioning dose. Administration of CFDA enhances immune response in a recipient in a dose-dependent manner.

10 Claims, 13 Drawing Sheets

COMPOSITION AND METHOD FOR MODULATING IMMUNE RESPONSIVENESS

BACKGROUND OF THE INVENTION

An immune system comprises a network of molecules and cells designed for a singular purpose, namely, to distinguish between self and nonself. As a protector against viral, bacterial, and parasitic pathogens, the immune system relies on two strategies to react to countless molecular entities and initiate destruction of the entities identified as foreign bodies. The first strategy is the humoral immune response, dedicated to a recognition role through plasma cell-derived antibodies. The second strategy is the cellular immune response, dedicated to the eradication of cells displaying foreign motifs on their surfaces.

Local immuno-inflammatory processes involve a series of changes that include at least three steps: 1) peripheral blood leukocytes adhere to the endothelial wall and become fully activated; 2) the leukocytes migrate toward the inflammatory site; and 3) phagocytosis and, eventually, bacterial killing takes place. These processes are mediated by molecules known as selectins and integrins (Springer, 1995). CD11b is an integrin that is particularly relevant in bacteria-induced inflammatory processes. It is constitutively expressed on phagocytes, T- and B-cell subsets and natural killer (NK)/cytotoxic cells in several species (McFarland et al., 1992; Muto et al., 1993; Ross et al. 1993; Hasslen et al, 1996).

CD11b has at least three major functions in association with leukocytes. In lymphocytes, it is required for adhesion to the endothelium (Buysmann et al., 1997), then it is required for migration, and later, it mediates adhesion to parasites (Forsyth et al., 1996; Forsyth et al., 1997). In phagocytes, CD11b mediates diapedesis of leukocytes through the endothelium via generation of a high-affinity binding site for intercellular adhesion molecule-1 (Hogg et al., 1995; Sugimori et al., 1997). CD11b also mediates phagocytic and degranulation responses to bacteria or immune complexes opsonized with iC3b (Petty et al., 1993; Sutterwala et al., 1996). Most of the CD11b contained in leukocytes is not expressed on the membrane, but is stored in intra-cytoplasmic granules. Upon stimulation with cytokines (IL-1, TNF-$\alpha$), cell activating agents such as endotoxin, bacteria, or parasites induce an increase in CD11b expression, derived from intra-cytoplasmic CD11b (Ross et al., 1993; Hasslen et al., 1996). Not surprisingly, increases in CD11b receptor density have been reported in inflammatory diseases (Tsutsui et al., 1999). In *S. aureus* infections, expression of CD11b is positively correlated with bacterial clearance (Gordon et al., 1989; Inoue et al., 1998) and it has been shown that CD11b contains multiple sites for binding microbes (Ross et al., 1985).

CD11b is a molecule essential in leukocyte activation, leukocyte migration from peripheral blood or tissue to the inflammatory site, and phagocytosis (Ross et al., 1985; Petty and Todd, 1993; Hogg and Berlin, 1995). The use of fluorescent beads allows for flow cytometric evaluation of phagocytosis (Miyauchi et al., 1998). In addition, flow cytometry can quantify the number of each leukocyte type based on scatter light measurements. Inoculation of viable, but not infective, *S. aureus* into the peritoneum induces a local inflammation which results in a cell infiltrate collectable through peritoneal lavage.

Lymphocytes differ functionally over their lifetime. While thymic and peripheral blood T-lymphocytes are regarded as unprimed or naive cells (i.e., cells not exposed to foreign substances such as invading bacteria), lymphocytes found at local sites (i.e., mammary gland) are "memory" or "effector" cells that have been exposed to specific foreign antigens and are permanently capable of responding to them. This difference is reflected in the lymphocyte phenotype: unprimed or naive cells are predominantly CD45r positive (higher receptor density per cell) while memory or effector cells are predominantly CD45r negative (Taylor et al., 1994).

Bovine mastitis is typically a local inflammatory process of the udder associated with bacterial invasion, and *Staphylococcus aureus* is one such etiologic agent. While prevention or decreased prevalence of bovine mastitis would be facilitated by enhancing a local immune response, testing of putative immuno-modulatory therapies is frequently limited by the cost and logistical needs of in vivo studies. Thus, development and evaluation of new models of bovine mastitis is a pre-condition for selection of products that later may be evaluated in the bovine species, as well as for potency monitoring of products used to prevent bovine mastitis.

Validation of successful models must fulfill several conditions. First, a desirable model should include variables directly relevant to those present in bovine mastitis. One such set of variables comprises indicators of leukocyte activation, migration, and phagocytosis. Second, a model and its procedures should be accurate, repeatable, economical and capable of being rapidly tested. While in vitro models may meet several criteria, in certain circumstances they lack variables of biological relevance. However, the goal of biological relevance and the criteria indicated are met through the implementation of an in vivo model.

SUMMARY OF THE INVENTION

The present invention relates to a composition and method for non-specific enhancement of immune responses. A colostrum-derived dietary supplement (CDDS) is described for human or veterinary use. CDDS comprises a sprayed-dried preparation of pasteurized and homogenized first milking colostrum that when administered orally enhances immune responses in a recipient human or animal. Generally, CDDS is administered in a conditioning dose once per day during a conditioning period of time from about 7 to 14 days, and then in a maintenance dose administered once per day during a period that follows the conditioning period. The maintenance dose is about one-half the concentration of the conditioning dose. Administration of CDDS enhances the immune response in a recipient in a dose-dependent manner, and has been shown to effectively result in an increase in the expression of CD11b positive receptors on blood lymphocytes, an increase in CD11b receptor density on blood lymphocytes, an increase in the expression of CD4 positive receptors on lymphocytes, enhancement of leukocyte activation in a recipient, an increase in phagocytic function in macrophage cells, an increase in phagocytic function in polymorphonuclear (PMN) cells, an increase in the expression of activated PMN cells, and an increase in the expression of CD11b positive PMN cells.

The present invention will become apparent to those skilled in the art upon reference to the following specification, figures, and claims.

DETAILED DESCRIPTION OF THE INVENTION

Figure 1:
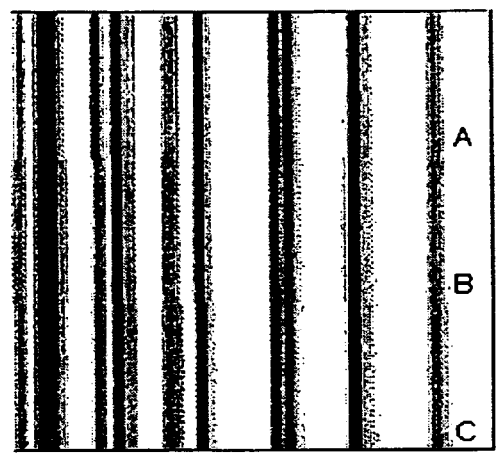
FIG. 1: Identification of *S. aureus* strains by automated riboprinting. A: One-day post-infection isolate from Animal No. 6271; B: One-day post-infection isolate from Animal No. 6288; C: *S. aureus* stock.

As stated above, the present invention is a colostrum-derived composition and method for administering the same to achieve non-specific enhancement of immune responses in human and animal recipients.

Preparation Colostrum-Derived Dietary Supplement (CDDS) Composition

First milking colostrum is obtained from Grade A dairy herds. New two-gallon polyethylene jugs are provided for saving first milking colostrum from healthy cows during their third or subsequent lactation. Freshly milked colostrum is inspected for quality and then placed in a freezer and maintained at −5° F.+/−5° F.

The frozen colostrum is next thawed at room temperature for 16–38 hours. Target batch sizes are based upon yields of approximately 1.9 lbs of spray-dried colostrum powder per 1.0 gallon of colostrum.

Thawed colostrum is evaluated with a clean hydrometer to measure specific gravity. The minimum acceptable value is 1.042 g/ml. The pH is then determined. The acceptable range is 5.0–7.0. Colostrum appearing watery or thin is rejected and discarded. Accepted colostrum is pooled by pouring through a stainless screen into a holding tank. A sample of the raw pooled colostrum is then at −5° F.+/−5° F. Accepted colostrum is passed through a specialized high temperature/short time pasteurizer and homogenizer (156° F.+/−1° F. (1200/300) lbs and directed into a tank. During the preparation process, all liquids are transported by pneumatic pumps with food grade bellows. The pH and volume of each lot is recorded.

Next, the pooled colostrum is treated by addition of 5% $H_2O_2$ solution to achieve a product concentration of 0.075% and preserved as described below. The product is then cooled and maintained at 37° F.+/−5° F. A sample of the product is taken and a portion used for total aerobic colony count (must be 10,000 CFU/ml). The remaining sample is retained frozen.

To produce a powdered composition, a spray-drying unit (Niro Atomizer S12.5Rn-GC-2 with rotary atomizer and vacuum powder conveying system) is operated according to the manufacturers instructions with the following parameters: inlet temperature of 450–470°, outlet temperature of 165–185° F. (maintained by feeding the liquid product at a rate of approximately 80 liters per hour) and cyclone differential pressure drop of 6–8 inches of water corresponding to 666–700 SCFM air rate. The colostrum powder is collected by a vacuum conveying system, sifted into fiber drums lined with 3 mm polyethylene bags, and sealed with self-locking nylon ties. Uniform size samples are taken from each finished drum for quality control testing and as retention samples. After all testing is complete, an approved batch is eligible for compounding as described below. After the entire batch has been dried, the dryer is dry-cleaned to remove virtually all powder residues. If necessary, the drying chamber is washed with chlorinated caustic solution and rinsed with dilute phosphoric acid.

Potassium sorbate is used to preserve the product and is added directly to the warm production lot under agitation, at 50% w/w solution to achieve a batch concentration of 0.125% (1.25 grams/liter). For example, first calculate the weight of potassium sorbate (50%) needed to preserve 5,000 liters of colostrum to achieve a batch concentration of 0.125% (1.25 grams/liter). Assuming a 5,000 liter batch, the following values would be appropriate: 5,000 liter×1.25 g/l potassium sorbate=6,250/5004=12,500 grams of 50% w/w solution added to the warm colostrum pool under agitation.

Batch samples are pooled and a composite evaluated as described below. The percent of first milking bovine colostrum total protein is adjusted for a given serial through mixing with whey powder. For example: calculate the weight of colostrum powder and whey powder needed to produce a serial of 2,000 total lbs; the percent first milking bovine colostrum powder total protein of finished product is 1.25%; percent total protein of first milking bovine colostrum powder is 50.0%; 1.25% protein/50% total protein of colostrum powder=2.5%. Assuming a target serial size of 2,000 lbs: 2,000 pounds finished product×2.5% colostrum powder=50 lbs colostrum powder and 2,000 lbs finished product–50 lbs colostrum powder=1,950 lbs whey powder. The 50 lbs of colostrum powder is sifted (if not previously done during preparation) with the 1,950 lbs of whey powder into a ribbon blender and mixed thoroughly. The resulting product is packaged in fiber drums lined with 3 mm polyethylene bags or 1 gallon plastic pails lined with 3 mm resealable bags to the desired net weight. The volume of the average serial is 80 drums of 25 lbs each (2,000 lbs) or 400 pails of 5 lbs each (2,000 lbs) or any combination thereof. The volume of the maximum serial is 2,125 lbs or 85 drums of 25 lbs each.

Tests for bacterial contamination are performed as outlined below. Reconstitute 1 gram of colostrum powder by mixing with 99 ml of distilled water or Butterfield's Buffer. A solution of reconstituted colostrum powder prepared in this manner is used for all purity testing.

Aerobic Count

Prepare serial dilutions of sample. Vortex each for ten seconds. Dispense 1 ml of appropriate diluent into aerobic counting plates. Incubate plates at 35+/−2° C. for 48 hours. Count colonies and report as CFU's per gram. Colony counts of less than 100,000 CFU's/gram result in a serial that meets the requirements for total aerobic count. Positive and negative controls are run concurrently.

Coliforms

Dispense 1 ml of appropriate diluent into Petrifilm Coliform count plates or equivalent. Incubate plates at 35+/−2° C. for 24 hours. Observe. Confirm suspicious colonies by Enterotube II or equivalent testing. The serial passes if no coliforms are found. Positive and negative controls are run concurrently.

Salmonellae

Dispense 1 ml of solution into a 100×15 mm petri dish and add 10–15 ml of brilliant greenagar that has been fluidized at 45–50° C. Rotate the petri dish gently to mix and allow the mixture to solidify. Incubate plates at 35+/−2° C. for 24 hours. Confirm suspicious colonies by Enterotube II or equivalent testing. The serial passes if no salmonellae are found. Positive and negative controls are run concurrently.

Fungi

Dispense 1 ml of solution into Petrifilm Yeast and Mold count plates or equivalent. Incubate plates at 23+/−2° C. for 5 days. Observe. The serial passes if <200 CFU/gram found. Positive and negative controls are run concurrently.

Oral administration of the composition in a dose of 12 grams per day for the first fourteen days, then reducing to 6 grams per day for continuous feeding has been shown to prevent and/or ameliorate mastitis in the lactating bovine.

EXAMPLE 1

Measurement of CD11b allows the identification of leukocyte activation (i.e., early immune responses) and, in addition, the magnitude of CD11b expression is thought to correlate with bacterial clearance (i.e., preventing bacteria from establishing an infection or by eliminating the infection more rapidly).

Relevant lymphocyte markers other than CD11b are CD4 and CD8. Lymphocytes bearing CD8 are more predominant than CD4 T-cells in the milk of healthy cows (Taylor et al., 1994). Thus, an increased CD4/CD8 ratio indicates immuno-modulation.

CD45r is a marker that distinguishes naive cells from memory or effector cells (Taylor et al., 1994). Naive cells are lymphocytes that have not been exposed to the bacterial antigen and therefore, require more time to mount an effective immune response. Assessment of this marker provides an indirect estimate of the functional status of lymphocytes (naive/memory cell ratio).

Materials and Methods

Animals

Two groups of five (5) first-lactation, non-periparturient heifers were recruited from the herds at the College of Agriculture, Cornell University. All animals used in the study were certified free of disease and in good health by a qualified veterinarian. During the study, the animals were separated from the main herds and kept in a controlled environment. The animals were housed, fed, and milked according to federal and university regulations (Protocol 543/98, Cornell University).

Treatment

Colostrum-Derived Feed Additve (CDFA), a dried form of first milking bovine colostrum produced as described above, was incorporated into the total mixed rations fed daily to one group of five (5) heifers. Each animal recipient received a daily conditioning dose of 12 grams per day for fourteen (14) consecutive days prior to intra-mammary bacterial inoculation. A maintenance dose of 6 grams per day per animal was included in the daily rations thereafter. The remaining group of five (5) heifers served as controls.

Experimental Infection and Bacteriological Monitoring

*Staphylococcus aureus*, ribotype 116-232-S3 (Rivas, et al. Diversity of *Streptococcus agalactiae* and *Staphylococcus*

*aureus* Ribotypes Recovered from New York Dairy Herds, *Am J Vet Res* 1997; 58:482–487) was cultured in Todd-Hewitt broth at 37° C., a measurement of colony-forming units (CFU) was made, and the organisms were resuspended in the same medium at a dilution of 150–200 CFU/ml, and refrigerated until infused. *Staphylococcus aureus*, ribotype 116-232-S3 is an isolate from a commercial New York dairy farm. After the morning milking, 150–200 CFU/ml of this strain were inoculated into each of the right front and left hind quarters of each udder of the treated and control animals. After infusion, a sample of the inoculum was cultured onto blood agar (100 μl per plate) and bacterial colonies quantified following incubation for 24 hours at 37° C. Verification of the *S. aureus* strain was performed by automated ribotyping of isolates as described by Rivas (Rivas et al., 1997). Each experimental and control animal was tested no fewer than four times: before the experimental inoculation (pre-i), at one day post-inoculation (1 dpi), at one week post-inoculation (1 wpi) and at two weeks post-inoculation (2 wpi).

Somatic Cell Counts (SCC)

Milk SCC was performed with a Fossomatic Cell Counter at the Dairy Herd Improvement Association (DHIA) laboratory in Ithaca, N.Y.

Isolation of Lymphocytes From Milk

At least 2 liters of milk from the morning milking of the right front and left hind quarters were collected in disinfected milking containers. The milk samples were transported at 4° C. in sterile 1-liter bottles containing 10 ml (100×) of antibiotic-antimycotic and gentamicin (12.5 ug/ml). Milk processing began within 1 hr post-collection. Milk samples were diluted with an equal volume of PAE buffer (PBS+10% acid citrate dextrose+20 mM EDTA) and centrifuged at 1500 rpm at 15° C. for 40 minutes. The supernatant and fat layer were removed, and the cell pellet was washed three times with PAE buffer. The cell pellet was resuspended in 30 ml of HBSS and layered on Percoll by infusing a gradient medium underneath. It was then centrifuged at 2400 rpm at 15° C. for 30 minutes. Leukocytes were then collected, washed three times in 10% fetal bovine serum (FBS)-HBSS and resuspended in 5 ml of complete medium [RPMI, 10% $FBS^c$, and 5% of a tissue culture mixture containing 100 ml of non-essential amino acids solution (10 mM), 100 ml L-glutamine (200 mM), 100 ml sodium pyruvate, and 100 ml Hepes buffer]. Cells were then counted and cell viability was estimated.

Isolation of Lymphocytes From Peripheral Blood

Approximately 15 ml of blood was collected from the tail vein of an animal into heparinized tubes and transported at 4° C. The cellular components of the whole blood were separated by low speed centrifugation and white blood cells were collected. The white blood cells were layered on a Ficoll gradient and centrifuged at 1500 rpm at 15° C. for 45 minutes. The cell pellet (enriched for mononuclear cells) was harvested, washed, and counted.

Immunophenotyping of Lymphocyte Cell Surface Markers

Monoclonal antibodies against bovine cell surface receptors for CD3 (a T-lymphocyte marker), CD4, CD8, CD45r, and CD11b were purchased from VMRD (Pullman, Wash.). Six million lymphocytes were centrifuged at 1500 rpm for 10 minutes in first wash buffer, which contained 2% rabbit serum diluted in PAE buffer, pH 7.2 (PBS with 0.1% $NaN_3$, 10% citrate, 2% 10 nM EDTA per 100 ml). One million leukocytes were then transferred to 12×75 mm polypropylene tubes (one tube for each primary antibody including the isotype control) and resuspended in 50 μl of 10% rabbit serum (a blocking step to prevent Fc receptor and non-specific binding). After 10 minutes on ice, 50 μl of isotype control or monoclonal antibody was added to each tube and incubated on ice for an additional 30 minutes. The cells were washed three times and then incubated with 100 μl of the secondary antibody (FITC-conjugated rabbit anti mouse IgG [H&L chains] in 10% rabbit serum). Cells were then washed four times, fixed in 500 μl of 2% formaldehyde PBS-azide, refrigerated, kept in darkness, and analyzed with a fluorescence-activated flow cytometer (FACSCalibur, Becton-Dickinson, CA). In all tests, bovine leukocytes were isolated, immunobound, and fixed within twelve hours of collection. Fluorescence data were acquired and analyzed with CELLQuest software (Becton-Dickinson, CA). Gates for each leukocyte type were customized each testing day to achieve the lowest non-specific fluorescence and the highest specific fluorescence. To acquire enough cells of the leukocyte type least represented in each sample, a minimum of 40,000 leukocyte events were acquired per sample.

Statistical Analysis

Parametric and non-parametric analyses were conducted with commercially available statistical software (Minitab, State College, Pa.).

Results

Assessment of Bacterial Strains

In the reported results, the same *S. aureus* strain was recovered from infected animals. Thus, differences reported are not attributable to bacterial strain diversity (FIG. 1).

Relationships Between SCC, Bacteriology, and Leukocyte Differential Counts

The total post-inoculation SCC of the treated group ($22.673 \times 10^3$ cells/ml, right front and left hind quarters) represented 56% of the total SCC of the control group ($40.687 \times 10^3$ cells/ml). The median post-inoculation SCC/ml was 403,000 in untreated animals, and 243,000 in treated animals (left hind quarters), and 101,000 and 72,000 SCC/ml in the right front quarters of untreated and treated animals, respectively. However, the reported differences did not reach statistical significance. In contrast, the total bacterial count (CFU/ml) (163,013 for untreated animals; and 65,851 for treated animals), was significantly lower in treated animals ($p<0.01$, $\chi^2$ test, Table 1). Three treated animals (Nos. 6301, 6321, and 6378) showed bacterial clearance in previously positive quarters. In contrast, no untreated animal showed bacterial clearance after *S aureus* had been isolated (Table 1).

TABLE 1

RELATIONSHIP BETWEEN $SCC^a$ AND MILK BACTERIOLOGY

| | | | $Culture^b$ | | $SCC^a$ | |
|---|---|---|---|---|---|---|
| | Animal # | Test Time | $LRQ^c$ | $RFQ^d$ | LRQ | RFQ |
| Treatment Group | 6271 | pre-inoculation (pre-i) | 0 | 0 | $17^e$ | $17^e$ |
| | 6271 | 1 day post-inoculation (dpi) | 0 | 1 | $1904^e$ | $1904^e$ |

TABLE 1-continued

RELATIONSHIP BETWEEN SCC[a] AND MILK BACTERIOLOGY

| | | | Culture[b] | | SCC[a] | |
|---|---|---|---|---|---|---|
| | Animal # | Test Time | LRQ[c] | RFQ[d] | LRQ | RFQ |
| | 6271 | 1 week post-inoculation (wpi) | 0 | 0 | 166[e] | 166[e] |
| | 6271 | 2 wpi | 10[e] | 10[e] | 36[e] | 36[e] |
| | 6295 | pre-i | 0 | 0 | 34 | 35 |
| | 6295 | 1 dpi | 0 | 0 | 17 | 27 |
| | 6295 | 1 wpi | 0 | 0 | 93 | 19 |
| | 6295 | 2 wpi | 0 | 0 | 16 | |
| | 6301 | pre-i | 0 | 0 | 37 | 18 |
| | 6301 | 1 dpi | 8880 | 3250 | 39 | 40 |
| | 6301 | 1 wpi | 10000 | 0 | 516 | 356 |
| | 6301 | 2 wpi | 10000 | 0 | 1615 | 72 |
| | 6321 | pre-i | 0 | 0 | 172 | 62 |
| | 6321 | 1 dpi | 1730 | 5690 | 10 | 16 |
| | 6321 | 1 wpi | 280 | 50 | 272 | 285 |
| | 6321 | 2 wpi | 3600 | 0 | 1160 | 1385 |
| | 6378 | pre-i | 0 | 0 | 22 | 8 |
| | 6378 | 1 dpi | 0 | 10160 | 8198 | 67 |
| | 6378 | 1 wpi | 1710 | 500 | 267 | 367 |
| | 6378 | 2 wpi | 0 | 10000 | 243 | 3370 |
| Median[f] | | | 0 | 0 | 243 | 72 |
| Total | | | 36210 | 29661 | 14552 | 8121 |
| Control Group (Untreated) | 6236 | pre-i | 0 | 0 | 21[e] | 21[e] |
| | 6236 | 1 dpi | 0 | 0 | 403 | 403 |
| | 6236 | 1 wpi | 0 | 0 | 420 | 420 |
| | 6236 | 2 wpi | 0 | 0 | 65 | 65 |
| | 6273 | pre-i | 0 | 0 | 58 | 27 |
| | 6273 | 1 dpi | 0 | 0 | 713 | 27 |
| | 6273 | 1 wpi | 0 | 0 | 193 | 78 |
| | 6273 | 2 wpi | 0 | 0 | 70 | 41 |
| | 6288 | pre-i | 0 | 0 | 47[e] | 47[e] |
| | 6288 | 1 dpi | 680 | 2470 | 25 | 22 |
| | 6288 | 1 wpi | 33200 | 150 | 8013 | 4946 |
| | 6288 | 2 wpi | 100000 | 860 | 1803 | 1103 |
| | 6358 | pre- | 0 | 0 | 12 | 18 |
| | 6358 | 1 dpi | 0 | 3 | 12 | 61 |
| | 6358 | 1 wpi | 4840 | 530 | 80 | 101 |
| | 6358 | 2 wpi | 2320 | 490 | 1626 | 2909 |
| | 6360 | pre-i | 0 | 0 | 66 | 122 |
| | 6360 | 1 dpi | 120 | 210 | 343 | 5 |
| | 6360 | 1 wpi | 3740 | 2530 | 5226 | 1306 |
| | 6360 | 2 wpi | 870 | 10000 | 7547 | 2661 |
| Median[f] | | | 120 | 150 | 403 | 101 |
| Total | | | 145770 | 17243 | 26539 | 14148 |

[a]somatic cell count (1 × 10$^3$ cells/ml)
[b]colony forming units/ml
[c]left rear quarter
[d]right front quarter
[e]composite sample (left rear and right front quarters)
[f]post-inoculation (n = 15 observations per group)
[Note: No significant difference was observed in the total leukocyte concentration between experimental and control animals at any testing interval (Table 2)]

TABLE 2

TOTAL PERIPHERAL BLOOD AND MILK[a] LEUKOCYTE CONCENTRATION

| | Animal # | Pre-i[b] | 1 dpi[c] | 1 wpi[d] | 2 wpi[d] |
|---|---|---|---|---|---|
| Milk Cells (millions/liter) | | | | | |
| Treated | 6271 | 5.0 | 74.0 | 20.0 | 7.5 |
| | 6295 | 2.8 | 4.0 | 9.0 | 10.5 |
| | 6301 | 5.0 | 12.5 | 41.0 | 75.0 |
| | 6321 | 1.7 | 2.5 | 29.0 | 42.0 |
| | 6378 | 2.8 | 170.0 | 31.0 | 336.0 |
| Control | 6236 | 6.0 | 40.0 | 10.5 | 11.0 |
| | 6273 | 6.6 | 12.8 | 19.0 | 17.5 |
| | 6288 | 3.8 | 6.8 | 22.0 | 22.0 |
| | 6358 | 7.5 | 4.0 | 27.0 | 16.0 |
| | 6360 | 3.0 | 5.75 | 420.0 | 284.0 |
| Blood cells (millions/ml) | | | | | |
| Treated | 6271 | 1.7 | 1.23 | 1.0 | 0.6 |
| | 6295 | 1.7 | 1.47 | 2.4 | 2.0 |
| | 6301 | 4.3 | 4.30 | 2.7 | 2.4 |

TABLE 2-continued

TOTAL PERIPHERAL BLOOD AND MILK[a] LEUKOCYTE CONCENTRATION

|         | Animal # | Pre-i[b] | 1 dpi[c] | 1 wpi[d] | 2 wpi[d] |
|---------|----------|----------|----------|----------|----------|
|         | 6321     | 2.4      | 3.10     | 2.9      | 5.0      |
|         | 6378     | 3.1      | 0.82     | 1.7      | 1.3      |
| Control | 6236     | 0.5      | 0.44     | 0.6      | 1.6      |
|         | 6273     | 3.1      | 3.70     | 2.8      | 3.0      |
|         | 6288     | 2.2      | 1.05     | 0.9      | 2.0      |
|         | 6358     | 1.4      | 2.50     | 2.8      | 2.0      |
|         | 6360     | 2.6      | 2.70     | 2.8      | 1.3      |

[Note:
[a]composite of two (left hind and right front) quarters;
[b]pre-inoculation;
[c]day post-inoculation;
[d]week post-inoculation milk cells (millions/liter)]

Relationships Among Leukocyte Phenotypes

Figure 2A:
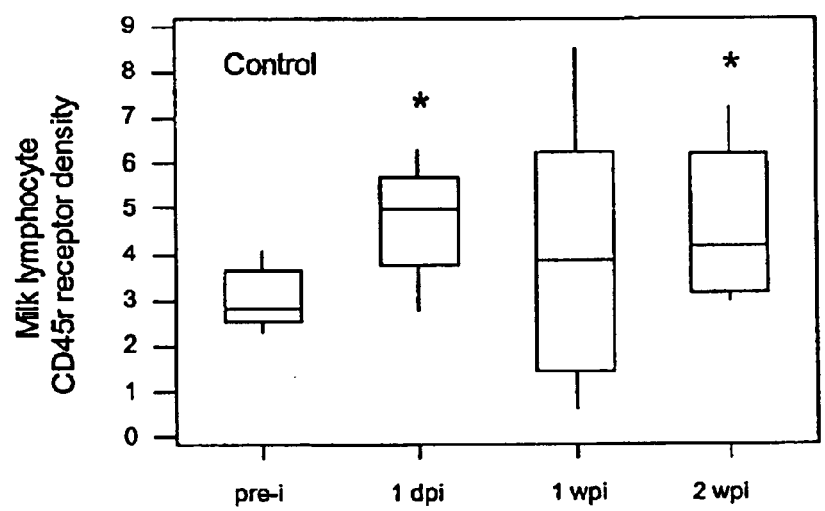
FIG. 2: Milk lymphocyte CD45r receptor density. Box plots represent the median and 95% distribution of 5 animals each. Control animals showed significant post-challenge increases (*) at 1 day post-inoculation (1 dpi) and 2 weeks post-inoculation (2 wpi), compared to pre-inoculation (pre-i). In contrast, treated animals did not show post-challenge differences.
Figure 2B:
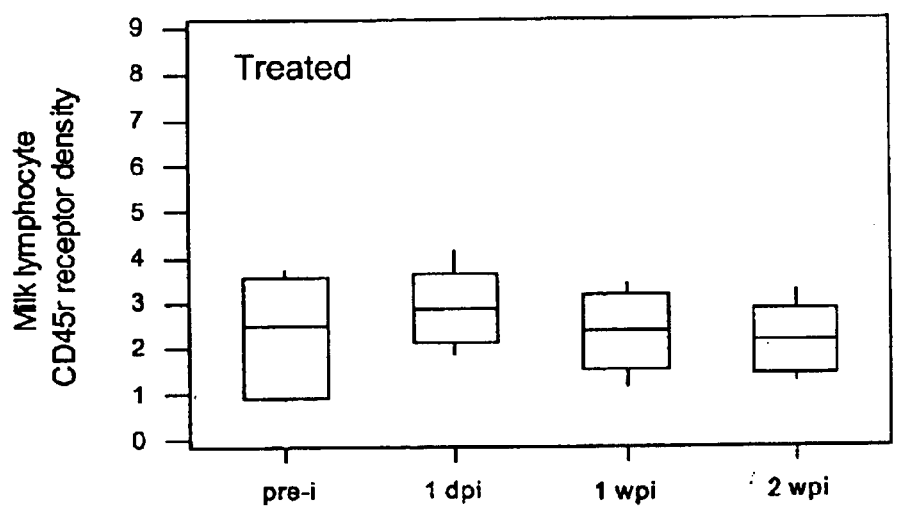

Proxy measurements for leukocyte function were based on evaluations of cell surface markers. No differences in the percent of blood CD3+ lymphocytes between treated and control animals were found at 1 dpi in treated animals. However, a significant increase of CD3+ lymphocytes was observed after challenge in control animals (Table 3). This change was associated with a significant increase in the milk lymphocyte CD45r receptor density of control animals (p=0.03, Table 4, FIG. 2).

TABLE 3

CD3+ LYMPHOCYTE PERCENTAGE

|             | Animal No. | Pre-i[a] | 1 dpi[b]* | 1 wpi[c] | 2 wpi |
|-------------|------------|----------|-----------|----------|-------|
| Blood Cells |            |          |           |          |       |
| Treated     | 6271       | 71.6     | 62.3      | 77.1     | 28.9  |
|             | 6295       | 56.1     | 58.2      | 74.6     | 61.2  |
|             | 6301       | 65.2     | 62.2      | 65.8     | 77.5  |
|             | 6321       | 61.9     | 66.7      | 70.0     | 72.2  |
|             | 6378       | 76.3     | 55.8      | 68.7     | 69.3  |
| Control     | 6236       | 67.0     | 86.1      | 76.1     | 77.9  |
|             | 6273       | 73.4     | 76.2      | 69.9     | 58.3  |
|             | 6288       | 64.9     | 62.5      | 67.2     | 69.4  |
|             | 6358       | 74.0     | 72.5      | 79.0     | 69.6  |
|             | 6360       | 64.2     | 54.0      | 61.1     | 54.4  |
| Milk Cells  |            |          |           |          |       |
| Treated     | 6271       | 78.2     | 67.8      | 91.6     | 95.2  |
|             | 6295       | 70.6     | 53.3      | 87.2     | 69.0  |
|             | 6301       | 59.2     | nt        | 61.1     | 72.5  |
|             | 6321       | nt       | 69.8      | 84.2     | 78.1  |
|             | 6378       | nt       | 23.8      | 93.1     | 65.7  |
| Control     | 6236       | 56.1     | 90.3      | 75.7     | 85.4  |
|             | 6273       | 69.5     | 90.4      | 90.9     | nt    |
|             | 6288       | 71.8     | 72.6      | 73.1     | 63.6  |
|             | 6358       | 95.0     | 84.4      | 88.9     | 91.5  |
|             | 6360       | 83.6     | 67.7      | 66.5     | 88.1  |

[Note:
[a]pre-inoculation;
[b]day post-inoculation;
[c]week post-inoculation;
*Control animals showed a significantly greater milk CD3+ lymphocyte percent (p = 0.03, Mann-Whitney test)].

TABLE 4

CD45r MILK LYMPHOCYTE MEDIAN FLUORESCENCE INTENSITY

|         | Animal No. | Pre-i[a] | 1 dpi[b]* | 1 wpi[c] | 2 wpi* |
|---------|------------|----------|-----------|----------|--------|
| Treated | 6271       | 0.86     | 4.17      | 2.91     | 3.23   |
|         | 6295       | 3.72     | 1.88      | 1.15     | 1.30   |
|         | 6301       | 0.98     | 2.37      | 3.42     | 2.47   |
|         | 6321       | 2.50     | 2.84      | 2.36     | 1.56   |
|         | 6378       | 3.39     | 3.11      | 1.84     | 2.18   |
| Control | 6236       | 2.81     | 4.78      | 8.51     | 7.23   |
|         | 6273       | 2.74     | 6.29      | 3.99     | 5.18   |
|         | 6288       | 3.16     | 5.13      | 2.29     | 4.21   |
|         | 6358       | 4.07     | 2.76      | 3.87     | 3.34   |
|         | 6360       | 2.31     | 4.98      | 0.60     | 2.99   |

[Note:
[a]pre-inoculation;
[b]day post-inoculation;
[c]week post-inoculation;
*Control animals exhibited greater receptor density than Treated animals (p < 0.03, Mann-Whitney test)].

Figure 3:
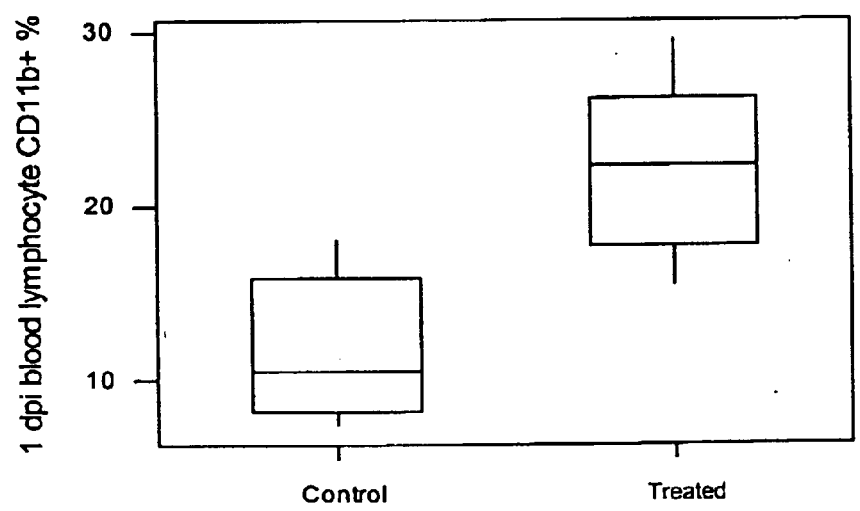
FIG. 3: CD11b+ blood lymphocyte percent at one day post-inoculation (1 dpi). Box plots represent the median and 95% distribution of 5 animals each. Treatment with the colostrum-derived dietary supplement (CDDS) is associated with a statistically significant (p=0.04) post-challenge increase of CD11b+ lymphocyte percentage.
Figure 4:
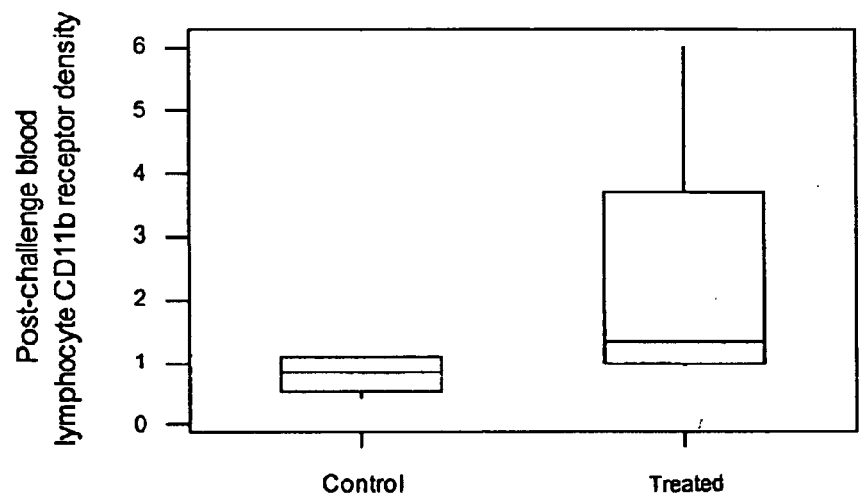
FIG. 4: CD11b receptor density per blood lymphocyte after challenge (ratio of 1 week post-inoculation/pre-inoculation). Box plots represent the median and 95% distribution of 5 animals each. Treatment with CDDS is associated with a significant (p=0.04) post-challenge increase of CD11b receptor density per lymphocyte.

Both the percent and median receptor density per cell of CD11b+ blood lymphocytes increased significantly in treated animals between 1 dpi and 1 wpi (p<0.04, Tables 5, 6 and FIGS. 3,4). The fluorescence percent of CD11b+ blood lymphocytes at 1 dpi and mean fluorescence percent between 1 dpi and 1 wpi were higher in treated animals in a statistically significant manner. However, at 1 dpi, the milk lymphocyte CD11b percent and the lymphocyte CD11b receptor density did not differ between groups.

TABLE 5

BLOOD AND MILK CD11b+ LYMPHOCYTE PERCENTAGES

|             | Animal # | Pre-i[a] | 1 dpi[b]* | 1 wpi[c] | Ratio 1 dpi/1 wpi[d]* | 2 wpi |
|-------------|----------|----------|-----------|----------|-----------------------|-------|
| Blood cells |          |          |           |          |                       |       |
| Treated     | 6271     | 9.8      | 22.8      | 19.9     | 21.4                  | 39.9  |
|             | 6295     | 19.7     | 29.6      | 8.5      | 19.1                  | 19.7  |
|             | 6301     | 13.3     | 15.5      | 28.1     | 21.8                  | 6.3   |
|             | 6321     | 25.9     | 20.0      | 19.0     | 19.5                  | 13.8  |
|             | 6378     | 1.7      | 22.3      | 8.0      | 15.2                  | 7.9   |
| Control     | 6236     | 11.8     | 9.1       | 14.6     | 11.9                  | 6.4   |
|             | 6273     | 11.5     | 10.5      | 15.8     | 13.2                  | 18.6  |
|             | 6288     | 12.9     | 13.8      | 11.2     | 12.5                  | 4.0   |
|             | 6358     | 7.5      | 7.4       | 6.8      | 7.1                   | 10.1  |
|             | 6360     | 13.0     | 18.0      | 12.0     | 15.0                  | 25.8  |
| Milk cells  |          |          |           |          |                       |       |
| Treated     | 6301     | 1.5      | 8.3       | 17.0     | 12.7                  | 9.7   |
|             | 6271     | 0.8      | 31.8      | 3.8      | 17.8                  | 1.7   |
|             | 6295     | 1.2      | 4.0       | 1.6      | 2.8                   | 10.3  |
|             | 6321     | 0.3      | 3.3       | 5.7      | 4.5                   | 20.7  |
|             | 6378     | 1.1      | 72.7      | 2.9      | 37.8                  | 21.0  |
| Control     | 6236     | 0.6      | 13.3      | 15.3     | 14.3                  | 3.4   |
|             | 6273     | 1.2      | 3.3       | 1.6      | 2.5                   | 2.9   |
|             | 6288     | 0.9      | 1.1       | 9.6      | 5.4                   | 10.8  |
|             | 6358     | 4.7      | 6.4       | 3.9      | 5.2                   | 2.5   |
|             | 6360     | 0.9      | 13.8      | 33.8     | 23.8                  | 15.8  |

[Note:
[a]pre-inoculation;
[b]day post-inoculation;
[c]week post-inoculation;
[d]1 dpi + 1 wpi/2;
*Treated animals showed greater percent of fluorescent blood cells than Control animals (p < 0.01, Mann-Whitney test)].

TABLE 6

BLOOD CD11b LYMPHOCYTE MEDIAN RECEPTOR DENSITY PER CELL

|  | Animal # | Pre-i[a] | 1 dpi[b] | 1 wpi[c] | Ratio 1 wpi/pre-i* | 2 wpi |
|---|---|---|---|---|---|---|
| Treated | 6271 | 0.92 | 2.22 | 5.53 | 6.01 | 3.16 |
|  | 6295 | 2.43 | 5.83 | 3.26 | 1.34 | 4.05 |
|  | 6301 | 3.16 | 3.48 | 4.53 | 1.43 | 2.55 |
|  | 6321 | 2.28 | 2.34 | 2.18 | 0.96 | 1.77 |
|  | 6378 | 1.90 | 1.75 | 1.91 | 1.01 | 2.33 |
| Control | 6236 | 3.64 | 4.39 | 4.04 | 1.11 | 3.71 |
|  | 6273 | 2.67 | 2.87 | 2.85 | 1.07 | 2.57 |
|  | 6288 | 2.64 | 2.77 | 1.22 | 0.46 | 1.34 |
|  | 6358 | 2.48 | 1.88 | 2.07 | 0.83 | 2.08 |
|  | 6360 | 2.76 | 2.11 | 1.73 | 0.63 | 2.93 |

[Note:
[a]pre-inoculation;
[b]day post-inoculation;
[c]week post-inoculation;
*Treated animals showed greater receptor density than Control animals (p < 0.04, Mann-Whitney test)].

Figure 5:
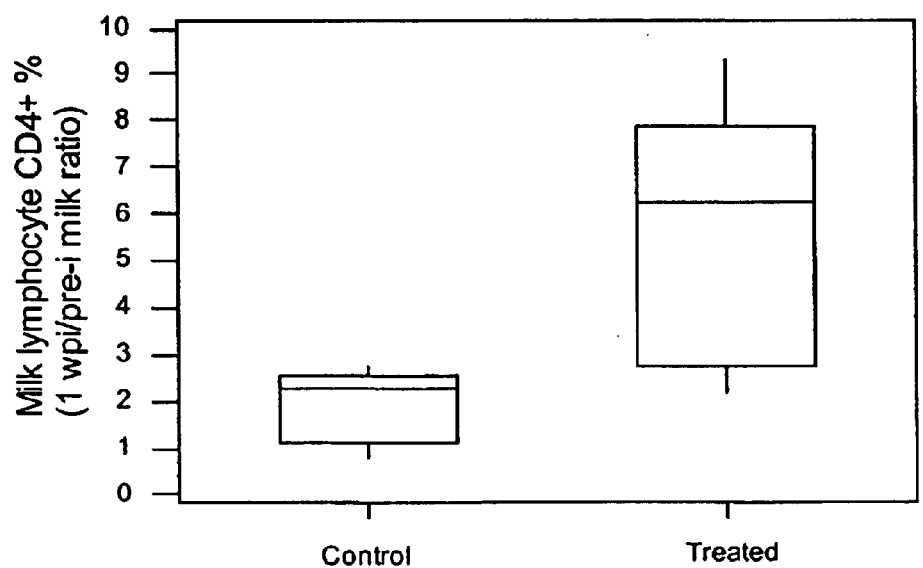
FIG. 5: Post-challenge milk lymphocyte CD4 percentage (one day post-inoculation/pre-inoculation). Box plots represent the median and 95% distribution of 5 animals each. Treatment with CDDS is associated with a significant (p=0.03) post-challenge increase of lymphocyte CD4+ percentage.
Figure 6:
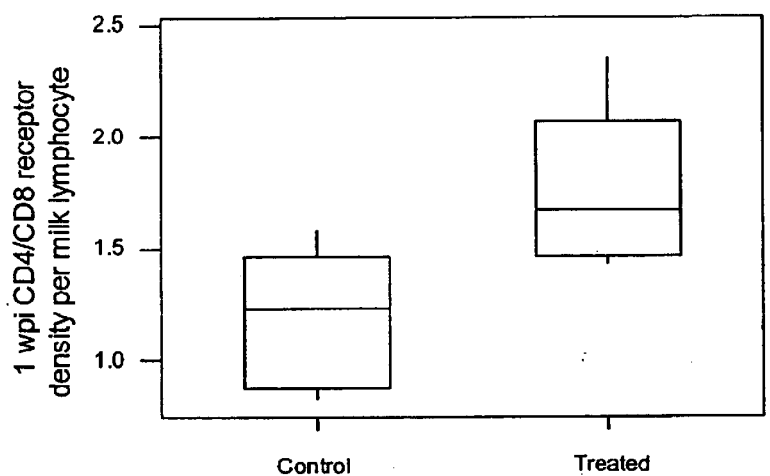
FIG. 6: Post-challenge milk lymphocyte CD4/CD8 receptor density ratio. Box plots represent the median and 95% distribution of 5 animals each. Treatment with CDDS is associated with a significant (p=0.02) post-challenge increase of CD4 receptor density per lymphocyte in comparison to that of CD8.

Milk CD4+ lymphocyte values increased more in treated animals than in untreated animals. This was shown as a significantly higher 1 wpi/pre-inoculation ratio of the milk CD4+ percent of treated animals (p=0.03). At the same post-infection time, the milk lymphocyte CD4/CD8 receptor density ratio increased significantly in treated animals (Tables 7, 8; FIGS. 5, 6).

TABLE 7

MILK CD4+ LYMPHOCYTE PERCENTAGE

|  | Cow # | Pre-i[a] | 1 dpi[b] | 1 wpi[c] | Ratio 1 wpi/Pre-i* | 2 wpi |
|---|---|---|---|---|---|---|
| Treated | 6271 | 9.4 | 36.0 | 31.5 | 3.35 | 17.4 |
|  | 6295 | 9.1 | 14.2 | 56.8 | 6.24 | 40.9 |
|  | 6301 | 16.0 | 28.3 | 34.5 | 2.16 | 35.4 |
|  | 6321 | 5.3 | 21.4 | 49.7 | 9.34 | 33.1 |
|  | 6378 | 7.9 | 10.5 | 50.7 | 6.42 | 31.0 |
| Control | 6236 | 12.5 | 28.2 | 17.3 | 1.38 | 13.5 |
|  | 6273 | 26.9 | 61.6 | 63.3 | 2.35 | 48.3 |
|  | 6288 | 15.7 | 29.3 | 43.3 | 2.76 | 38.4 |
|  | 6358 | 24.0 | 48.4 | 18.9 | 0.79 | 32.6 |
|  | 6360 | 19.6 | 25.3 | 44.8 | 2.28 | 39.1 |

[a]pre-inoculation;
[b]day post-inoculation;
[c]week post-inoculation;
*Treated animals showed greater 1 wpi/pre-inoculation ratio of milk CD4+ lymphocyte percent than Control animals (p = 0.03, Mann-Whitney test)

TABLE 8

RATIO OF MILK LYMPHOCYTE CD4/CD8 MEDIAN FLUORESCENCE INTENSITY

|  | Cow # | Pre-i[a] | 1 dpi[b] | 1 wpi[c]* | 2 wpi |
|---|---|---|---|---|---|
| Treated | 6271 | 1.00 | 2.00 | 1.78 | 1.74 |
|  | 6295 | 1.17 | 1.40 | 1.67 | 1.01 |
|  | 6301 | 1.54 | 1.65 | 2.35 | 1.63 |
|  | 6321 | 1.16 | 1.27 | 1.43 | 1.25 |
|  | 6378 | 0.87 | 2.34 | 1.49 | 1.91 |
| Control | 6236 | 0.83 | 2.00 | 0.82 | 0.84 |
|  | 6273 | 1.20 | 1.33 | 1.23 | 1.16 |
|  | 6288 | 1.40 | 1.31 | 1.58 | 1.31 |
|  | 6358 | 1.06 | 1.00 | 0.92 | 1.14 |
|  | 6360 | 1.30 | 1.35 | 1.34 | 2.95 |

[a]pre-inoculation;
[b]day post-innoculation;
[c]week post-inoculation;
*Treated animals showed greater receptor density than Control animals (p < 0.02, Mann-Whitney test)

Discussion

Assessments of SCC, Bacteriology, Total and Differential Leukocyte Counts

Statistically significant differences were not demonstrated between the treated and control groups in terms of total leukocyte concentration, leukocyte differential counts, and SCC. The same bacterial strain was found in milk isolates obtained after experimental infusion. Thus, the treatment was not associated with changes in cell morphology, the overall number of cells in the inflammatory response, or the bacterial strain. In contrast, the treatment was associated with lower bacterial counts (median CFU/ml per mammary gland quarter) and leukocyte phenotype changes.

Expression of CD11b

Several statistically significant immunophenotypic differences were found between treated and untreated animals. At early stages of the infection (between one day post-inoculation and one week post-inoculation) blood lymphocytes demonstrated activation at greater levels, both in terms of CD11b percent and CD11b median receptor density per cell, when comparing treated to untreated animals. Data demonstrating that blood lymphocytes exhibited an increased CD11b receptor density at 1 dpi, while milk lymphocytes exhibited no increase, suggests that the activation process, as reflected by CD11b receptor density, begins in blood, not in milk. This finding is consistent with reports demonstrating that expression of CD11b is a required step not only to facilitate cell adhesion, an intermediary step in the process of cell migration from the to peripheral blood capillary to the local inflammatory site such as the mammary gland, but also to phagocytize bacteria in conjunction with complement factors (Springer, 1995). In conjunction with the observed lower median CFU/ml of *S. aureus* found in milk of treated animals after challenge, and the lower median SCC measured in the same animals, it is suggested that heightened activation (i.e., more cells expressing CD11b or the same number of cells expressing CD11b at a higher receptor density per cell) is an immuno-modulatory effect that may be associated with more efficient cell migration and phagocytic function. The observed migrational and functional effect could ultimately be expressed as faster clearance of viable bacteria (i.e., lower CFU/ml), resulting in a subsequent reduction in inflammation (i.e., lower SCC). Thus, dietary supplementation with CDFA in animals with poor levels of constitutive immune activation may result in non-specific enhancement of their immune response. For example, animal no. 6301 (the animal showing the highest percent of CD11b+ blood lymphocytes at 1 wpi), animal no. 6321 (the animal showing the highest percent of CD11b+ blood lymphocytes at pre-inoculation), and animal no. 6378 (the animal showing the highest increase in CD11b+ blood lymphocyte percent between pre-inoculation and 1 dpi) demonstrated clearance of bacteria from the udder.

Expression of CD4 and CD8

A shift in the milk lymphocyte ratio from a CD8-predominant to a CD4-predominant ratio is a major hallmark of the initiation of the immune response. Treated animals showed both an increase in the number of CD4 molecules per cell (increased receptor density, expressed as a higher CD4/CD8 receptor density ratio) and a net increase in the percent of CD4+ milk lymphocytes. Thus, the data shows that there were more CD4+ lymphocytes and, on average, each lymphocyte expressed more CD4 receptors, when comparing treated to untreated animals. This finding is consistent with the observed heightened expression of CD11b, since it is expected that a greater level of cell activation at 1 dpi would be followed by a stronger CD4-mediated immune response. CD4+ lymphocytes, but not CD8+ T-cells, have been reported to be associated with clearance activity against several bacterial species (Kyd et al., 1999).

Expression of CD45r

A greater expression of CD45r on milk lymphocytes (naive phenotype) was observed in control animals when compared to treated animals. The observation that treated animals did not display naive phenotype is consistent with a local immune response directed to mounting faster anti-bacterial functions (i.e., with non-naive or memory cells).

Conclusions

Supplementation of the diet of lactating animals with CDFA was associated with a statistically significant modification of several immune markers (CD3, CD4, CD8, CD11b, CD45r) in the blood and/or milk between one day post-inoculation and one week post-inoculation of the udder with Staphylococcus aureus. Heightened activation of the host immune response, observed immediately after bacterial inoculation, coupled with a non-naive, predominantly helper lymphocyte response, observed between one-day and one-week post-inoculation, was associated with lower median bacterial counts and lower SCC in treated animals.

The data demonstrate that CDFA is an immuno-modulating agent, inclusion of which in to the diet of a lactating animal is an effective prophylactic/therapeutic means to ameliorate the incidence and severity of mastitis through non-specific enhancement of the host immune response. Non-specific immune enhancement is particularly applicable in animals exhibiting a low percentage of lymphoid cells with CD11b receptors or a low density of CD11b receptors per cell.

In particular, treatment with CDFA in animals experiencing intra-mammary inoculation with S. aureus was associated with the following: a statistically significant lower CD45r receptor density per milk lymphocyte (P<0.03, FIG. 2); a statistically significant greater percentage of CD11b+ blood lymphocytes (P=0.04, FIG. 3); a statistically significant greater CD11b receptor density per blood lymphocyte (P=0.04, FIG. 4); a statistically significant greater percentage of CD4+ milk lymphocytes (P=0.03, FIG. 5); and a statistically significant greater CD4 receptor density per milk lymphocyte than that of CD8 (P=0.02, FIG. 6).

EXAMPLE 2

Assessment of the Relationship Between CDFA Dosage and Immuno-Modulation

A study was conducted to ascertain the following: determine whether the immuno-modulatory effects were demonstrable in a dose-dependent fashion and could be confirmed when animals of different genetic lines and managed under different conditions were treated with CDFA; and assess new variables indicative of immune-function.

Materials and Methods

Animals

Five groups of three (3) first-lactation, non-periparturient heifers were purchased from diverse herds in the area of Ithaca, N.Y. All animals used in Example 2 were in good health and certified free of disease by a qualified veterinarian. The animals were brought to the facilities of the College of Veterinary Medicine, Cornell University. The subject animals were separated from the main herds and kept in a special facility with a controlled environment. Study animals were housed, fed, and milked according to U.S.D.A. and university regulations (Protocol 543/98, Cornell University).

Treatment

CDFA, a dried form of first milking bovine colostrum produced by a process as described above, was incorporated into the total mixed rations fed daily to four groups of three (3) heifers. One group of three (3) heifers was reserved as the untreated control group. Treated animals each received a daily conditioning dose of 1.2, 6, 12, or 60 grams of CDFA per day for fourteen (14) consecutive days prior to intra-mammary bacterial inoculation. A corresponding maintenance dose representing one-half of the conditioning dose (0.6, 3, 6, or 30 grams per day per animal) was included in the daily rations thereafter.

Experimental Infection and Bacteriological Monitoring

Staphylococcus aureus, ribotype 116-232-S3 (Rivas, et al. Diversity of Streptococcus agalactiae and Staphylococcus aureus Ribotypes Recovered from New York Dairy Herds, Am J Vet Res 1997; 58:482–487) was cultured in Todd-Hewitt broth at 37° C., a measurement of colony-forming units (CFU) was made, and the organisms were resuspended in the same medium at a dilution of 150–200 CFU/ml, and refrigerated until infused. Staphylococcus aureus, ribotype 116-232-S3 is an isolate from a commercial New York dairy farm. After the morning milking, 150–200 CFU/ml of this strain were inoculated into each of the right front and left hind quarters of an udder. After infusion, a sample of the inoculum was cultured onto blood agar (100 µl per plate) and bacterial colonies quantified following incubation for 24 hours at 37° C. Verification of the S. aureus strain was performed by automated ribotyping of isolates as described by Rivas (Rivas et al., 1997). Each experimental and control animal was tested before the experimental bacterial inoculation and on days 1, 2, 3 and 5 post-inoculation.

Somatic Cell Counts (SCC)

The milk SCC was determined with a Fossomatic Cell Counter at the Dairy Herd Improvement Association (DHIA) laboratory in Ithaca, N.Y.

Isolation of Lymphocytes From Peripheral Blood

Approximately 15 ml of blood was collected from the tail vein of an animal into heparinized tubes and transported at 4° C. The cellular components of the whole blood were separated by low speed centrifugation and white blood cells were collected. The white blood cells were layered on a Ficoll gradient and centrifuged at 1500 rpm at 15° C. for 45 minutes. The cell pellet (enriched for mononuclear cells) was harvested, washed, and counted.

Immunophenotyping of Lymphocyte Cell Surface Markers

Monoclonal antibodies against bovine cell surface CD3, CD11b receptors and isotype control were purchased from VMRD (Pullman, Wash.). Three million lymphocytes were centrifuged at 1500 rpm for 10 minutes in a first wash buffer containing 2% rabbit serum diluted in PAE buffer, pH=7.2

(PBS with 0.1% NaN$_3$, 10% citrate, 2% 10 nM EDTA per 100 ml). One million leukocytes were then transferred to 12×75 mm polypropylene tubes (one for each primary antibody including the isotype control) and resuspended in 50 μl of 10% rabbit serum (a blocking step that prevented Fc receptor and non-specific binding). After 10 minutes on ice, 50 μl of isotype control or monoclonal antibody was added to each tube and incubated for 30 minutes on ice. The cells were washed three times and then incubated with 100 μl of the secondary antibody (FITC-conjugated rabbit anti mouse IgG [H&L chains] in 10% rabbit serum). Cells were then washed four times, fixed in 500 μl of 2% formaldehyde PBS-azide, refrigerated, kept in darkness, and analyzed with a fluorescence-activated flow cytometer (FACSCalibur, Becton-Dickinson, CA). In all tests, bovine leukocytes were isolated, immunobound and fixed within twelve hours of being collected. Fluorescence data were acquired and analyzed with CELLQuest software (Becton-Dickinson, CA). Gates for each leukocyte type were customized each testing day to achieve the lowest non-specific fluorescence and the highest specific fluorescence. To acquire enough cells of the leukocyte type least represented in each sample, at least 40,000 leukocyte events were acquired per sample.

Sampling Scheme

Figure 7:
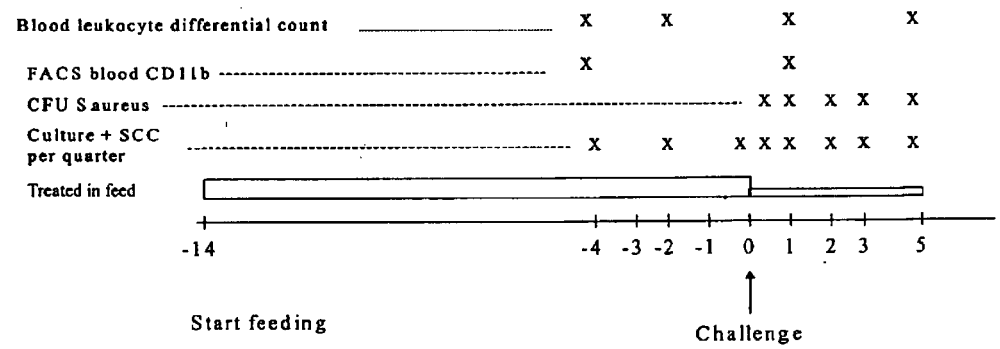
FIG. 7: Evaluations relating to Example 2 were conducted on samples collected according to the sampling scheme as shown.

Evaluations were conducted on samples collected according to the sampling scheme shown in FIG. 7.

Statistical Analysis

Parametric and non-parametric analyses were conducted with Statistics® statistical software.

Results

Assessment of Bacterial Strains

It was determined that the same *S. aureus* strain was recovered from each infected animal. Thus, differences reported are not attributable to bacterial strain diversity.

Relationship Between SCC and CDFA Dose

Figure 8:
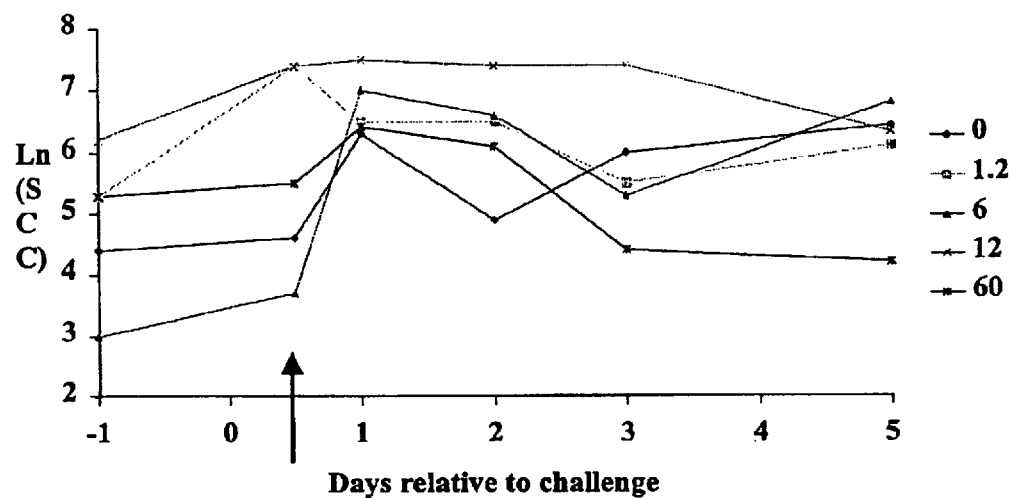
FIG. 8: Mean natural logarithm of SCC in relation to dose of CDDS (arrow indicates time of challenge).
Figure 9:
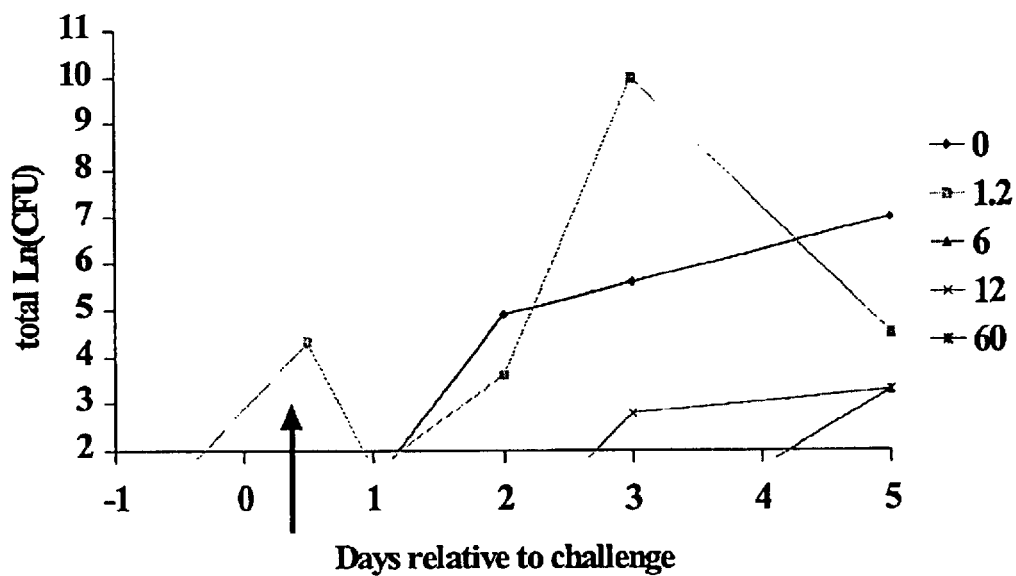
FIG. 9: Mean natural logarithm of CFU of *S. aureus* recovered in relation to dose of CDDS (arrow indicates time of challenge).

Table 9 is grouped according to the five doses evaluated in this trial and shows the results for each cow by individual quarters inoculated with *S. aureus*. While animals treated with CDFA showed increased SCC at some time after inoculation, the group treated with the highest dose (60/30 grams per cow per day) showed normal SCC (less than 500,000 SCC/ml) in each animal at three days post-infection. In contrast, all other groups showed [in at least one animal] longer inflammatory responses than that observed with the 60/30 gram per day dose. Thus, only the 60/30 gram dose group demonstrated a complete and rapid return to normal SCC values (Table 10). FIG. 8 provides a graphic representation of the mean SCC for each dosage group relative to the time of *S. aureus* challenge.

TABLE 9

SCC RELATIVE TO DOSE OF CDFA AND TIME OF CHALLENGE

| Animal # | Dose | Time (Days) | SCC (1 × 10³) LHQ | RHQ |
|---|---|---|---|---|
| 6208 | 0/0 | −1.0 | 57 | 45 |
| | | 0.5 | 63 | 77 |
| | | 1.0 | 148 | 167 |
| | | 2.0 | 43 | 52 |
| | | 3.0 | 816 | 67 |
| | | 5.0 | 2313 | 98 |
| 6262 | | −1.0 | 70 | 85 |
| | | 0.5 | 74 | 92 |
| | | 1.0 | 1224 | 229 |
| | | 2.0 | 925 | 82 |

TABLE 9-continued

SCC RELATIVE TO DOSE OF CDFA AND TIME OF CHALLENGE

| Animal # | Dose | Time (Days) | SCC LHQ | RHQ |
|---|---|---|---|---|
| | | 3.0 | 8471 | 204 |
| | | 5.0 | 3972 | 293 |
| 6346 | | −1.0 | 130 | 179 |
| | | 0.5 | 304 | 97 |
| | | 1.0 | 1616 | 2174 |
| | | 2.0 | 233 | 146 |
| | | 3.0 | 197 | 193 |
| | | 5.0 | 344 | 461 |
| 5420 | 1.2/0.6 | −1.0 | 164 | 238 |
| | | 0.5 | 261 | 795 |
| | | 1.0 | 207 | 185 |
| | | 2.0 | 618 | 187 |
| | | 3.0 | nd | nd |
| | | 5.0 | 2385 | 416 |
| 6193 | | −1.0 | 566 | 770 |
| | | 0.5 | 2826 | 10000 |
| | | 1.0 | 1438 | 2978 |
| | | 2.0 | 1116 | 6928 |
| | | 3.0 | 411 | 991 |
| | | 5.0 | 322 | 802 |
| 6487 | | −1.0 | 118 | 25 |
| | | 0.5 | 2659 | 1197 |
| | | 1.0 | 1407 | 463 |
| | | 2.0 | 77 | 1345 |
| | | 3.0 | 98 | 76 |
| | | 5.0 | 940 | 37 |
| Animal # | Dose | Time (Days) | SCC LHQ | RHQ |
| 6354 | 6/3 | −1.0 | 21 | 19 |
| | | 0.5 | 219 | 49 |
| | | 1.0 | 692 | 19839 |
| | | 2.0 | 823 | 5258 |
| | | 3.0 | 47 | 281 |
| | | 5.0 | 185 | 1003 |
| 6408 | | −1.0 | 43 | 24 |
| | | 0.5 | 26 | 63 |
| | | 1.0 | 393 | 470 |
| | | 2.0 | 257 | 372 |
| | | 3.0 | 17117 | 282 |
| | | 5.0 | 1923 | 6756 |
| 6413 | | −1.0 | 11 | 12 |
| | | 0.5 | 33 | 7 |
| | | 1.0 | 162 | 3615 |
| | | 2.0 | 1464 | 296 |
| | | 3.0 | 33 | 35 |
| | | 5.0 | 96 | 3269 |
| 3113 | 12/6 | −1.0 | 690 | 535 |
| | | 0.5 | 271 | 490 |
| | | 1.0 | 741 | 1383 |
| | | 2.0 | 868 | 534 |
| | | 3.0 | 682 | 1141 |
| | | 5.0 | 3876 | 418 |
| 4723 | | −1.0 | 252 | 361 |
| | | 0.5 | 1136 | 2310 |
| | | 1.0 | 1010 | 16169 |
| | | 2.0 | 702 | 3410 |
| | | 3.0 | 665 | 917 |
| | | 5.0 | 224 | 606 |
| 5272 | | −1.0 | 404 | 880 |
| | | 0.5 | 7585 | 7733 |
| | | 1.0 | 554 | 4771 |
| | | 2.0 | 3578 | 5631 |
| | | 3.0 | 4129 | 10000 |
| | | 5.0 | 287 | 36 |
| 3267 | 60/30 | −1.0 | 548 | 171 |
| | | 0.5 | 334 | 133 |
| | | 1.0 | 1093 | 3308 |
| | | 2.0 | 695 | 4036 |
| | | 3.0 | 29 | 180 |
| | | 5.0 | 21 | 177 |
| 5188 | | −1.0 | 296 | 314 |
| | | 0.5 | 1474 | 1277 |
| | | 1.0 | 87 | 171 |
| | | 2.0 | 107 | 107 |

TABLE 9-continued

SCC RELATIVE TO DOSE OF CDFA AND TIME OF CHALLENGE

|  |  |  |  |
|---|---|---|---|
|  | 3.0 | 62 | 70 |
|  | 5.0 | 90 | 39 |
| 5222 | −1.0 | 66 | 94 |
|  | 0.5 | 40 | 78 |
|  | 1.0 | 4020 | 270 |
|  | 2.0 | 2282 | 141 |
|  | 3.0 | 233 | 58 |
|  | 5.0 | 70 | 91 |

TABLE 10

SUMMARY OF SCC OBSERVATIONS

| Time (Days) | Quad | Dose 0/0 | 1 2/0 6 | 6/3 | 12/6 | 60/30 |
|---|---|---|---|---|---|---|
| −1.0 | Left | 85.7 | 282.7 | 25.0 | 448.7 | 303.3 |
|  | Right | 103.0 | 344.3 | 18.3 | 592.0 | 193.0 |
|  | Mean | 94.4 | 313.5 | 21.7 | 520.4 | 248.2 |
|  | Left | 147.0 | 1915.3 | 92.7 | 2997.3 | 616.0 |
|  | Right | 88.7 | 3997.3 | 39.7 | 3511.0 | 496.0 |
|  | Mean | 117.9 | 2956.3 | 66.2 | 3254.2 | 556.0 |
| 1.0 | Left | 996.0 | 1017.3 | 415.7 | 768.3 | 1733.3 |
|  | Right | 856.7 | 1208.7 | 7974.7 | 7441.0 | 1249.7 |
|  | Mean | 926.4 | 1113.0 | 4195.2 | 4104.7 | 1491.5 |
| 2.0 | Left | 400.3 | 603.7 | 848.0 | 1716.0 | 1028.0 |
|  | Right | 93.3 | 2820.0 | 1975.3 | 3191.7 | 1428.0 |
|  | Mean | 246.8 | 1711.9 | 1411.7 | 2453.9 | 1228.0 |
| 3.0 | Left | 3161.3 | 254.5 | 5732.3 | 1825.3 | 108.0 |
|  | Right | 154.7 | 533.5 | 199.3 | 4019.3 | 102.7 |
|  | Mean | 1658.0 | 394.0 | 2965.8 | 2922.3 | 105.4 |
| 5.0 | Left | 2209.7 | 1215.7 | 734.7 | 1462.3 | 60.3 |
|  | Right | 284.0 | 418.3 | 3676.0 | 461.3 | 102.3 |
|  | Mean | 1246.9 | 817.0 | 2205.4 | 961.8 | 81.3 |

Statistical analysis of SCC level at five days after challenge showed a linear decrease in SCC with an increasing dose of CDFA ($p<0.02$). The results of this analysis are shown in Table 11.

TABLE 11

UNWEIGHTED LEAST SQUARES LINEAR REGRESSION OF THE NATURAL LOGARITHM OF SCC AT 5 DAYS AFTER CHALLENGE

| PREDICTOR VARIABLES | COEFFICIENT | STD ERROR | STUDENT'S T | P |
|---|---|---|---|---|
| CONSTANT | 7.09003 | 0.43936 | 16.14 | 0.0000 |
| DOSE | −0.04353 | 0.01598 | −2.72 | 0.0174 |

| | | | | |
|---|---|---|---|---|
| R-SQUARED | 0.3634 | RESID MEAN SQUARE (MSE) | 1.93492 |
| ADJUSTED R-SQUARED | 0.3145 | STANDARD DEVIATION | 1.39102 |

| SOURCE | DF | SS | MS | F | P |
|---|---|---|---|---|---|
| REGRESSION | 1 | 14.3616 | 14.36160 | 7.42 | 0.0174 |
| RESIDUAL | 13 | 25.1540 | 1.93492 |  |  |
| TOTAL | 14 | 39.5156 |  |  |  |

CASES INCLUDED: 15   MISSING CASES 0

Relationship Between Bacterial Counts and CDFA Dose

The bacteriological results indicate that the three lowest doses of CDFA are associated with recovery of the inoculated bacteria (Table 12). The number of colony-forming units (CFU) of inoculated S.aureus that were cultured increased over time and there was no indication of spontaneous recovery, particularly in the untreated control animals. In contrast, in the 60/30 gram per day dosage group, no milk culture showed bacteriological growth at any time after challenge. Milk cultures from animals in the 6/3 gram per day group also showed very little growth of the challenge micro-organism. Thus, there was an associated bacterial clearance (or lack of actual infection) in treated animals.

TABLE 12

CFU Relative to Dose of CDFA and Time of Challenge

| Animal # | Dose | Time (Days) | CFU/ml LHQ | RHQ |
|---|---|---|---|---|
| 6208 | 0/0 | −1.0 | 0 | 0 |
|  |  | 0.5 | 0 | 0 |
|  |  | 1.0 | 0 | 0 |
|  |  | 2.0 | 0 | 0 |
|  |  | 3.0 | 870 | 0 |
|  |  | 5.0 | 4040 | 0 |
| 6262 |  | −1.0 | 0 | 0 |
|  |  | 0.5 | 0 | 0 |
|  |  | 1.0 | 50 | 0 |
|  |  | 2.0 | 4040 | 650 |
|  |  | 3.0 | 2180 | 10 |
|  |  | 5.0 | 670 | 520 |
| 6346 |  | −1.0 | 0 | 0 |
|  |  | 0.5 | 0 | 0 |
|  |  | 1.0 | 0 | 0 |
|  |  | 2.0 | 0 | 0 |
|  |  | 3.0 | 0 | 0 |
|  |  | 5.0 | 0 | 0 |
| 5420 | 1.2/0.6 | −1.0 | 0 | 0 |
|  |  | 0.5 | 0 | 0 |
|  |  | 1.0 | 0 | 0 |
|  |  | 2.0 | 0 | 0 |
|  |  | 3.0 | nd | nd |
|  |  | 5.0 | 0 | 0 |
| 6193 |  | −1.0 | 0 | 0 |
|  |  | 0.5 | 0 | 10 |
|  |  | 1.0 | 0 | 0 |
|  |  | 2.0 | 80 | 0 |
|  |  | 3.0 | 270 | 0 |
|  |  | 5.0 | 0 | 0 |
| 6487 |  | −1.0 | 0 | 0 |
|  |  | 0.5 | 3000 | 10 |
|  |  | 1.0 | 0 | 120 |
|  |  | 2.0 | 700 | 0 |
|  |  | 3.0 | 10000 | 190 |
|  |  | 5.0 | 10000 | 80 |
| 6354 | 6/3 | −1.0 | 0 | 0 |
|  |  | 0.5 | 0 | 0 |
|  |  | 1.0 | 0 | 0 |
|  |  | 2.0 | 0 | 0 |
|  |  | 3.0 | 0 | 0 |
|  |  | 5.0 | 0 | 0 |
| 6408 |  | −1.0 | 0 | 0 |
|  |  | 0.5 | 0 | 0 |
|  |  | 1.0 | 0 | 0 |
|  |  | 2.0 | 0 | 0 |
|  |  | 3.0 | 1240 | nd |
|  |  | 5.0 | 20800 | 0 |
| 6413 |  | −1.0 | 0 | 0 |
|  |  | 0.5 | 0 | 0 |
|  |  | 1.0 | 0 | 0 |
|  |  | 2.0 | 0 | 0 |
|  |  | 3.0 | 0 | 0 |
|  |  | 5.0 | 0 | 0 |
| 3113 | 12/6 | −1.0 | 0 | 0 |
|  |  | 0.5 | 0 | 0 |
|  |  | 1.0 | 0 | 0 |
|  |  | 2.0 | 0 | 0 |
|  |  | 3.0 | 4040 | 0 |
|  |  | 5.0 | 0 | 560 |
| 4723 |  | −1.0 | 0 | 0 |
|  |  | 0.5 | 0 | 0 |
|  |  | 1.0 | 0 | 0 |
|  |  | 2.0 | 0 | 0 |

TABLE 12-continued

CFU Relative to Dose of CDFA and Time of Challenge

| Animal # | Dose | Time (Days) | CFU/ml LHQ | CFU/ml RHQ |
|---|---|---|---|---|
| | | 3.0 | 0 | 0 |
| | | 5.0 | 40 | 0 |
| 5272 | | -1.0 | 0 | 0 |
| | | 0.5 | 0 | 80 |
| | | 1.0 | 0 | 0 |
| | | 2.0 | 0 | 0 |
| | | 3.0 | 0 | 0 |
| | | 5.0 | 0 | 0 |
| 3267 | 60/30 | -1.0 | 0 | 0 |
| | | 0.5 | 0 | 0 |
| | | 1.0 | 0 | 0 |
| | | 2.0 | 0 | 0 |
| | | 3.0 | 0 | 0 |
| | | 5.0 | 0 | 0 |
| 5188 | | -1.0 | 0 | 0 |
| | | 0.5 | 0 | 0 |
| | | 1.0 | nd | 0 |
| | | 2.0 | 0 | 0 |
| | | 3.0 | 0 | 0 |
| | | 5.0 | 0 | 0 |
| 5222 | | -1.0 | 0 | 0 |
| | | 0.5 | 0 | 0 |
| | | 1.0 | 0 | 0 |
| | | 2.0 | 0 | 0 |
| | | 3.0 | 0 | 0 |
| | | 5.0 | 0 | 0 |

Statistical analysis showed a negative trend with respect to dose of CDFA administered and the natural logarithm of CFU (colony forming units) of S. aureus recovered from the mammary glands of inoculated animals (p=0.0002). The results are shown in Table 13.

TABLE 13

UNWEIGHTED LEAST SQUARES LINEAR REGRESSION ANALYSIS OF THE NATURAL LOGARITHM OF TOTAL CFU

| PREDICTOR VARIABLES | CO-EFFICIENT | STD ERROR | STUDENT'S T | P | VIF |
|---|---|---|---|---|---|
| CONSTANT | 1.29952 | 0.55185 | 23.5 | 0.0209 | |
| DOSE | -0.04631 | 0.01643 | -2.82 | 0.0060 | 1.0 |
| TIME | 0.67369 | 0.18961 | 3.55 | 0.0006 | 1.0 |

| | | | | |
|---|---|---|---|---|
| R-SQUARED | | 0.1942 | RESID MEAN SQUARE (MSE) | 11.6594 |
| ADJUSTED R-SQUARED | | 0.1750 | STANDARD DEVIATION | 3.41458 |

| SOURCE | DF | SS | MS | F | P |
|---|---|---|---|---|---|
| REGRESSION | 2 | 235.974 | 117.9870 | 10.12 | 0.0002 |
| RESIDUAL | 84 | 979.386 | 11.6594 | | |
| TOTAL | 86 | 1215.36 | | | |

CASES INCLUDED 87   MISSING CASES. 3

Effect on WBC Differential Counts

Figure 10:
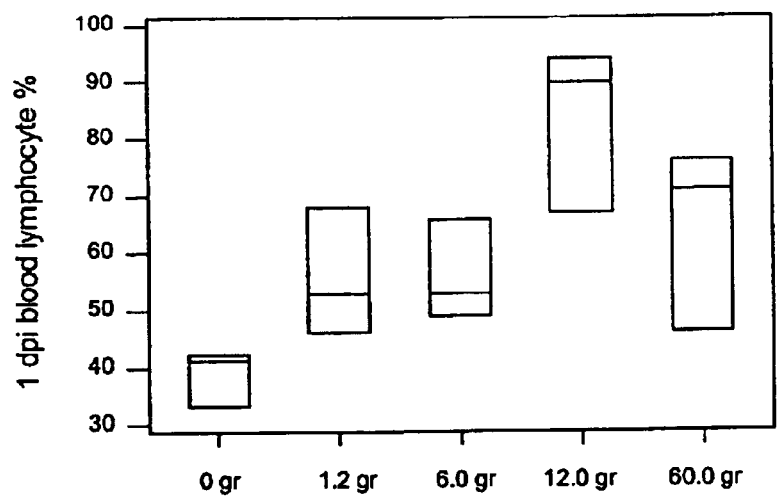
FIG. 10: Relationship between post-challenge blood lymphocyte percent and treatment. Bars represent the median and 95% distribution of 3 animals each. Treatment with CDDS is associated with a statistically significant 1 day post-inoculation (1 dpi) dose-dependent increase of lymphocyte percentage (p<0.007).
Figure 11:
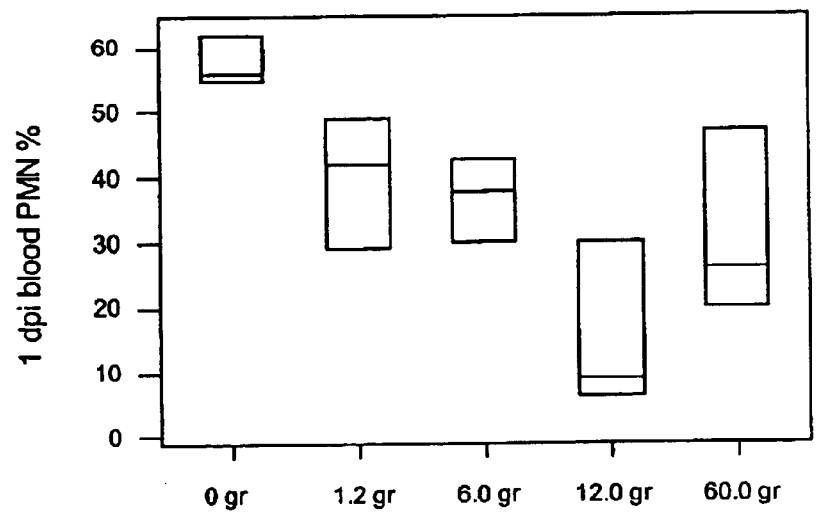
FIG. 11: Relationship between post-challenge blood PMN percent and treatment. Bars represent the median and 95% distribution of 3 animals each. Treatment with CDDS is associated with a statistically significant 1 day post-inoculation (1 dpi) dose-dependent decrease of PMN percentage (p<0.04).

All treated groups showed higher pre-challenge PMN percentages in blood than the PMN percent of the non-treated group at pre-challenge. While this trend seemed to be consistent, it did not reach statistical significance (Table 14). However, when comparing lymphocyte and PMN percentages significant differences were observed after challenge between the non-treated and some treated groups. The percentage of blood lymphocytes was 2-fold higher at 1 dpi in the 12.0 gram dose group when compared to the 0 gram group (p<0.007). In contrast, the percentage of blood PMN at 1 dpi was statistically lower in three dosage groups (6.0, 12.0 and 60.0 gm, p<0.04) when compared to the control group (FIGS. 10, 11). This indicates significant post-challenge dose-dependent responses for blood lymphocyte percentage, which increased in relation to dose, and granulocytes, which decreased in relation to dose. No significant differences were observed for monocytes.

TABLE 14

LEUKOCYTE DIFFERENTIAL COUNTS (%)

| Dose | Animal # | Pre-Inoculation PMN[c] | Pre-Inoculation L[d] | Pre-Inoculation M[e] | 1 day p-i[a] PMN | 1 day p-i[a] L | 1 day p-i[a] M | 1 week p-i[b] PMN | 1 week p-i[b] L | 1 week p-i[b] M |
|---|---|---|---|---|---|---|---|---|---|---|
| 0/0 | 6208 | 14 | 78 | 7 | 56 | 41 | 3 | 24 | 67 | 7 |
| | 6262 | 47 | 42 | 11 | 62 | 33 | 4 | 50 | 45 | 5 |
| | 6346 | 19 | 71 | 9 | 55 | 42 | 2 | 29 | 65 | 6 |
| | Mean | 26.7 | 63.7 | 9.0 | 57.7 | 38.7 | 3.0 | 34.3 | 59.0 | 6.0 |
| 1.2/0.6 | 5420 | 52 | 47 | 1 | 49 | 46 | 5 | 42 | 51 | 6 |
| | 6193 | 35 | 62 | 3 | 29 | 68 | 3 | 27 | 53 | 20 |
| | 6487 | 47 | 42 | 10 | 42 | 53 | 2 | 44 | 46 | 10 |
| | Mean | 44.7 | 50.3 | 4.7 | 40.0 | 55.7 | 3.3 | 37.7 | 50.0 | 12.0 |
| 6/3 | 6350 | 45 | 53 | 2 | 43 | 53 | 3 | 37 | 61 | 2 |
| | 6408 | 46 | 36 | 17 | 30 | 66 | 4 | 39 | 57 | 3 |
| | 6413 | 38 | 49 | 12 | 38 | 49 | 12 | 33 | 63 | 4 |
| | Mean | 43.3 | 46.0 | 10.3 | 37.0 | 56.0 | 6.3 | 36.3 | 60.3 | 3.0 |
| 12/6 | 3113 | 16 | 72 | 12 | 30 | 67 | 3 | 27 | 70 | 3 |
| | 4723 | 50 | 40 | 10 | 6 | 94 | 0 | 24 | 68 | 8 |
| | 5272 | 40 | 51 | 8 | 9 | 90 | 1 | 43 | 52 | 4 |
| | Mean | 35.3 | 54.3 | 10.0 | 15.0 | 83.7 | 1.3 | 31.3 | 63.3 | 5.0 |
| 60/30 | 5188 | 61 | 34 | 5 | 47 | 46 | 7 | 68 | 29 | 3 |
| | 5222 | 32 | 58 | 10 | 20 | 76 | 4 | 41 | 53 | 6 |

TABLE 14-continued

LEUKOCYTE DIFFERENTIAL COUNTS (%)

| | | Pre-Inoculation | | | 1 day p-i[a] | | | 1 week p-i[b] | | |
|---|---|---|---|---|---|---|---|---|---|---|
| Dose | Animal # | PMN[c] | L[d] | M[e] | PMN | L | M | PMN | L | M |
| | 3267 | 45 | 50 | 5 | 26 | 71 | 2 | 18 | 78 | 2 |
| | Mean | 46.0 | 47.3 | 6.7 | 31.0 | 64.3 | 4.3 | 42.3 | 53.3 | 3.7 |

[a]1 day post-inoculation;
[b]1 week (5–8 days) post-inoculation;
[c]polymorphonuclear leukocytes;
[d]lymphocytes; [e]monocytes.

Expression of CD11b Receptors on Blood Lymphocytes

Figure 12:
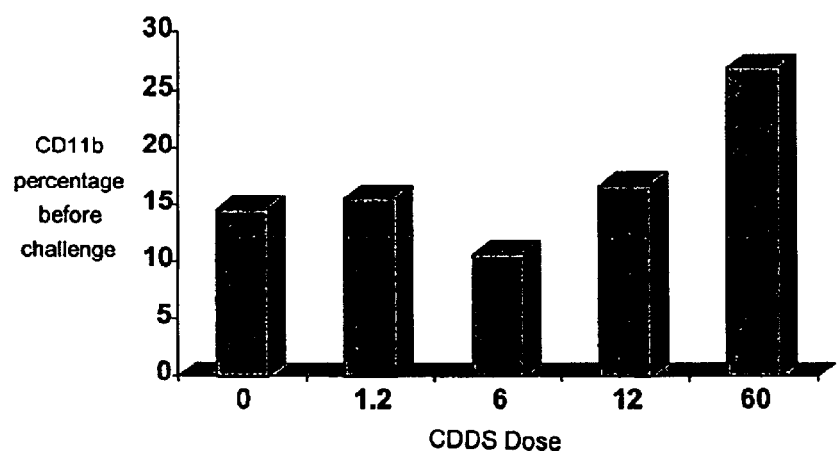
FIG. 12: Percent of CD11b+ blood lymphocytes before inoculation with *S. aureus*.

Before inoculation of *S. aureus* into the udder quadrants, the level of circulating lymphocytes expressing CD11b receptors was similar in animals receiving three of the four doses of CDFA (Table 15). However, before intra-mammary inoculation, animals receiving 60 grams per day of CDFA in their diet evidenced higher levels of circulating CD11b positive lymphocytes (FIG. 12). The observed difference was statistically significant (p=0.02, Mann-Whitney test).

TABLE 15

PERCENTAGE OF CD11b+ BLOOD LYMPHOCYTES AT PRE-
AND POST-INOCULATION WITH *S. AUREUS*

| | | % CD11b | | |
|---|---|---|---|---|
| Dose | Animal # | Pre-Inoc | Post-Inoc | % Change |
| 0/0 | 6208 | 14.70 | 24.30 | +65.31 |
| | 6262 | 10.80 | 16.10 | +49.07 |
| | 6346 | 18.40 | 19.30 | +4.89 |
| | Mean | 14.63 | 19.90 | +39.76 |
| 1.2/0.6 | 5420 | 10.70 | 8.60 | −19.63 |
| | 6193 | 23.50 | 24.30 | +3.40 |
| | 6487 | 12.50 | 12.50 | 0 |
| | Mean | 15.57 | 15.13 | −5.41 |
| 6/3 | 6354 | 6.10 | 12.50 | +104.92 |
| | 6408 | 15.00 | 39.80 | +165.33 |
| | 6413 | 10.60 | 15.30 | +44.34 |
| | Mean | 10.57 | 22.53 | +104.86 |
| 12/6 | 3113 | 35.80 | 44.90 | +25.42 |
| | 4723 | 9.60 | 2.70 | −71.88 |
| | 5272 | 4.60 | 13.80 | +200.00 |
| | Mean | 16.67 | 20.47 | +51.18 |
| 60/30 | 3267 | 24.30 | 49.00 | +101.65 |
| | 5188 | 15.40 | 26.20 | +70.13 |
| | 5222 | 41.00 | 54.80 | +33.66 |
| | Mean | 26.90 | 43.33 | +68.48 |

Figure 13:
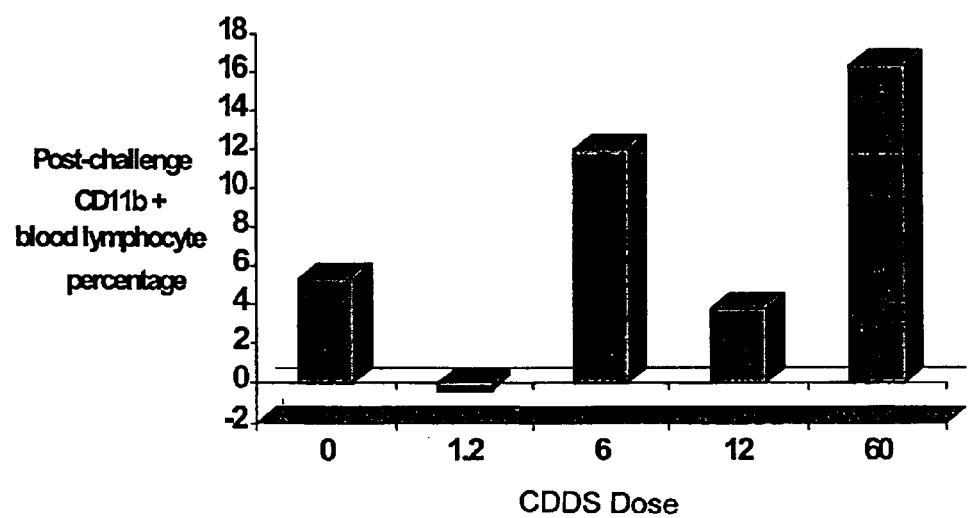
FIG. 13: Percent of CD11b+ blood lymphocytes after challenge with *S. aureus*.

After challenge, the percentage of CD11b+ cells increased in all groups, but approached statistical significance in only the highest dosage group [60/30 gram per day] (P=0.06; paired t test). However, when results are observed relative to the pre-challenge level, giving consideration to the post-challenge/pre-challenge index, animals in the 6/3 grams per day group showed the highest increase. This observation appears to be related to the fact that animals in the 6/3 grams per day group evidenced a more substantial increase in CD11b+ cells than that observed in animals given 0, 1.2/0.6 or 12/6 grams per day, while the pre-challenge level of CD11b+ cells in animals receiving the 6/3 grams per day dose was not significantly different than that seen in the other dosage groups. Regression analysis indicated a statistically significant relationship between dose and response (P=0.04; FIG. 13, Table 16).

TABLE 16

UNWEIGHTED LEAST SQUARES LINEAR REGRESSION OF
DIFFERENCE IN CD11b EXPRESSION POST-
INOCULATION OF *S. AUREUS*

| PREDICTOR VARIABLES | CO-EFFICIENT | STD ERROR | STUDENT'S T | P |
|---|---|---|---|---|
| CONSTANT | 4.17040 | 2.47329 | 1.69 | 0.1156 |
| DOSE | 0.20431 | 0.08994 | 2.27 | 0.0407 |
| R-SQUARED | | 0.2842 | RESID. MEAN SQUARE (MSE) | 61.3163 |
| ADJUSTED R-SQUARED | | 0.2291 | STANDARD DEVIATION | 7.83047 |

| SOURCE | DF | SS | MS | F | P |
|---|---|---|---|---|---|
| REGRESSION | 1 | 316.438 | 316.438 | 5.16 | 0.0407 |
| RESIDUAL | 13 | 797.112 | 61.3163 | | |
| TOTAL | 14 | 1113.55 | | | |

CASES INCLUDED 15   MISSING CASES

Figure 14:
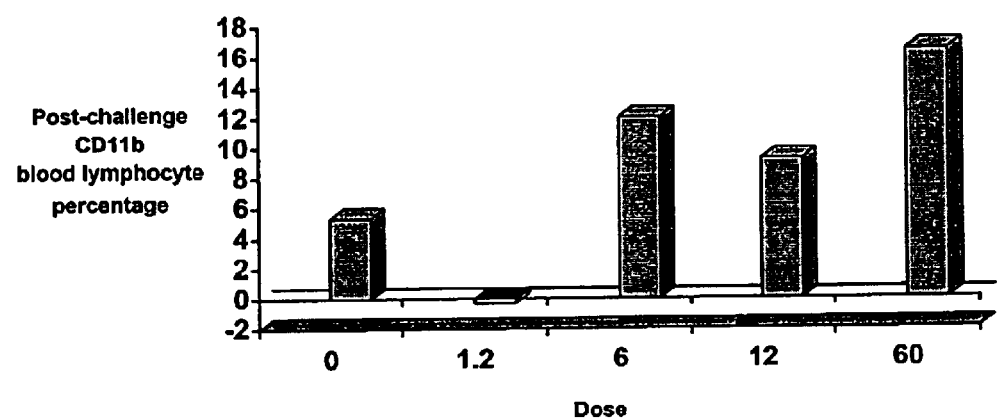
FIG. 14: Percent of CD11b+ blood lymphocytes after challenge with *S. aureus* (Animal No. 4723 removed).

However, one animal in the dosage group initially receiving 12 grams of CDFA per day and subsequently receiving 6 grams daily was an outlier. For unknown reasons, animal No. 4723 demonstrated responses that were unlike the responses of the 7 remaining animals (from Example 1 and Example 2) treated with the same dose. An interval (with 99% Confidence) of the responses of the other 7 animals exhibited a lower limit above the values exhibited by animal No. 4723 (Table 17). With statistical confidence of 99%, the response observed from animal no. 4723 was dissimilar the extent to which it was not considered for further analysis. When data derived from this animal were removed from analysis, the response in terms of an increase in CD11b expression on blood lymphocytes after challenge evidenced a stronger relationship to the dose of CDFA administered. The revised analysis is indicated as a lower P value (P=0.03; FIG. 14, Table 18).

TABLE 17

INTERVAL (99% CONFIDENCE) OF ALL 12/6 GM/DAY ANIMALS
(COW 4723 EXCLUDED)

Upper Limit: 38.88
Lower Limit:  9.38

TABLE 18

UNWEIGHTED LEAST SQUARES LINEAR REGRESSION OF DIFFERENCE IN CD11b EXPRESSION POST-INOCULATION OF S. AUREUS (ANIMAL 4723 REMOVED)

| PREDICTOR VARIABLES | CO-EFFICIENT | STD ERROR | STUDENT'S T | P |
|---|---|---|---|---|
| CONSTANT | 5.25478 | 2.30102 | 2.28 | 0.0414 |
| DOSE | 0.19696 | 0.08135 | 2.42 | 0.0323 |

| | | | | |
|---|---|---|---|---|
| R-SQUARED | | 0.3282 | RESID MEAN SQUARE (MSE) | 50.0662 |
| ADJUSTED R-SQUARED | | 0.2722 | STANDARD DEVIATION | 7.07575 |

| SOURCE | DF | SS | MS | F | P |
|---|---|---|---|---|---|
| REGRESSION | 1 | 293.454 | 293.4540 | 5.86 | 0.0323 |
| RESIDUAL | 12 | 600.794 | 50.0662 | | |
| TOTAL | 13 | 894.249 | | | |

| CASES INCLUDED | 14 | MISSING CASES | 0 |
|---|---|---|---|

Figure 15:
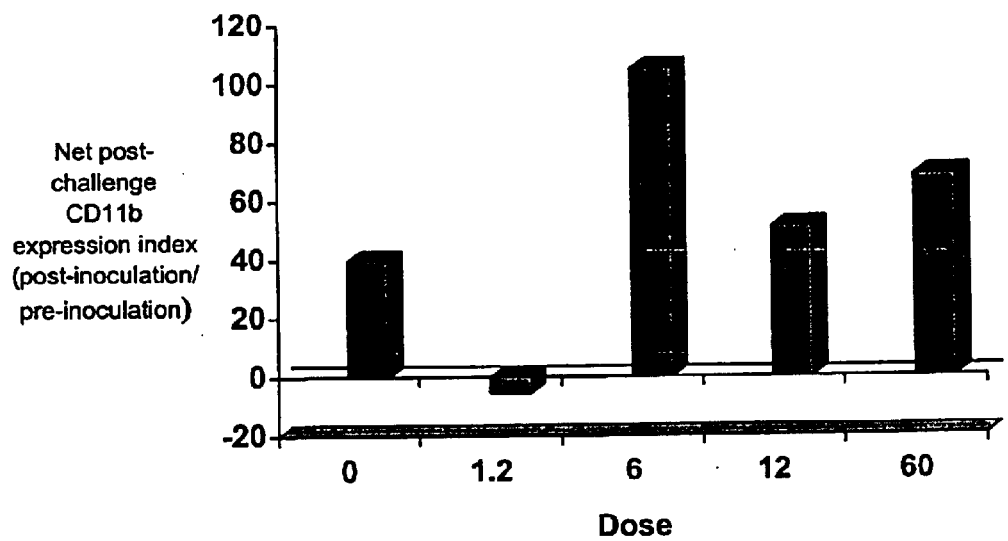
FIG. 15: Post-inoculation/pre-inoculation CD11b+ blood lymphocyte percent index.
Figure 16:
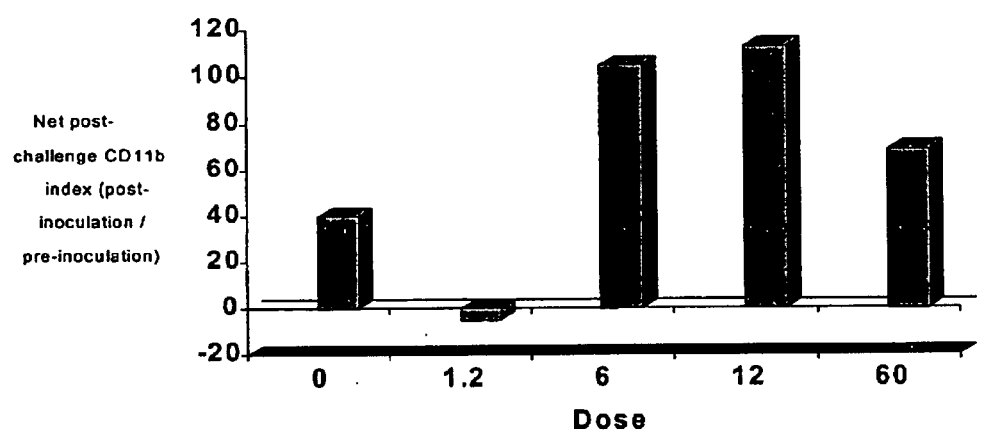
FIG. 16: Post-inoculation/pre-inoculation CD11b+ blood lymphocyte percent index (Animal No. 4723 removed).

Analysis of data expressed as a ratio between post-inoculation/pre-inoculation values allows for control of pre-inoculation animal variation. This ratio or index indicates that the largest change was observed in animals treated with the 60/30 grams dosage (Table 19, FIG. 15). However, when the data was analyzed absent the responses elicited from animal No. 4723, the highest response was seen in animals treated with the 12/6 grams dosage. This apparent shift is compounded by the high pre-inoculation values observed in the 60/30 grams dosage group which result in a lower index for this group (FIG. 16).

TABLE 19

NET POST-CHALLENGE CD11b+ BLOOD LYMPHOCYTE EXPRESSION IN RELATION TO DOSE OF CDFA

| | | % CD11b | |
|---|---|---|---|
| Dose | Cow # | Difference* | Change** |
| 0/0 | 6208 | 9.60 | 65.31 |
| | 6262 | 5.30 | 49.07 |
| | 6346 | 0.90 | 4.89 |
| | Mean | 5.27 | 39.76 |
| 1.2/0.6 | 5420 | 0 | — |
| | 6193 | 0.80 | 3.40 |
| | 6487 | 0 | — |
| | Mean | 0.27 | 3.40 |
| 6/3 | 6354 | 6.40 | 104.92 |
| | 6408 | 24.80 | 165.33 |
| | 6413 | 4.70 | 44.34 |
| | Mean | 11.97 | 104.86 |
| 12/6 | 3113 | 11.10 | 115.63 |
| | 4723*** | — | — |
| | 5272 | 9.20 | 200.00 |
| | Mean | 10.15 | 157.82 |
| 60/30 | 3267 | 24.70 | 101.65 |
| | 5188 | 10.80 | 70.13 |
| | 5222 | 13.80 | 33.66 |
| | Mean | 16.43 | 68.48 |

*Difference between post-inoculation minus pre-inoculation blood lymphocyte CD11b+ percentages;
**Change percent (post-/pre-inoculation values × 100);
***Values for Cow #4723 not tested since analysis indicated it was an outlier.

Discussion

The data generated in Example 2 further confirm the observations made in first-lactation periparturient heifers in Example 1. It was again demonstrated that inclusion of CDFA in an animal diet results in a greater percentage of CD11b positive lymphocytes in the blood following intra-mammary challenge with a viable strain of Staphylococcus aureus. These findings clearly indicate that CDFA is an immuno-modulating biological agent. In addition, two new indications of immuno-modulation were observed: a) statistically significant increases in blood lymphocyte percentages were found in treated cows at one day post-bacterial inoculation; and b) significant decreases of blood granulocytes were shown in treated cows at one day after challenge. Increases in lymphocyte counts in healthy subjects have been reported after physical exercise and exogenously supplied hormone treatments. (Hinrichsen et al., 1992, Kappel et al., 1998).

The present study provides five lines of evidence of dose-dependent immuno-modulatory effects. First, the increases observed in post-challenge lymphocyte values in treated animals followed a dose-dependent relationship. Second, the decrease in granulocyte values observed in the same animals also followed a dose-related response. Third, the increase in CD11b positive blood lymphocytes values demonstrated a statistically significant dose relationship as shown by linear regression analysis, whether considered alone as a one day post-inoculation percentage, or when considered as the ratio of post-challenge/pre-challenge CD11b expression, which controls against pre-challenge animal variation. Fourth, the post-challenge somatic cell counts remained high throughout the investigational period, both in controls and animals receiving the lowest doses, suggesting that the inflammatory process might last beyond five days post-challenge. In contrast, the highest dose was associated with a return to normal somatic cell values within three days post-challenge and followed a significant linear relationship as demonstrated by regression analysis. Fifth, regression analysis indicated a significant relationship (p=0.0002) between bacterial counts in milk and dosage of CDFA. Animals in the lowest CDFA dosage groups showed post-challenge bacteriological growth in milk cultures, while no bacterial recovery was observed in association with the highest dose (60/30 grams).

These data indicate that the optimum pre-challenge dose is between 6.0 and 12 grams per day.

Conclusions

Supplementing the daily diet of animals with CDFA for two weeks prior to challenge with a viable strain of Staphylococcus aureus and thereafter with a lesser daily dose is associated with immuno-modulatory effects that result in the following dose-dependent response after challenge with Staphylococcus aureus: a statistically significant linear negative relationship between SCC values and dose (i.e., the higher the dose, the lower the SCC, P=0.017, Table 11); a statistically significant linear negative relationship between bacterial counts and dose (P=0.006, Table 13); a statistically significant positive relationship between blood lymphocyte percentage and dose (i.e., the greater the dose, the higher the lymphocyte percentage, P<0.007, FIG. 10); a statistically significant negative relationship between blood granulocytes and dose (P<0.04, FIG. 11); and a statistically significant positive relationship between CD11b positive blood lymphocyte percentage and dose (P<0.05, Tables 17 and 18).

EXAMPLE 3

Assessment of Combined Data From Examples 1 and 2

Example 1 is directed primarily to examining the influence of CDFA on the immune response of the lactating bovine following intra-mammary challenge with Staphylococcus aureus. Example 1 utilized, a group of five (5) animals derived from the herd at the College of Veterinary Medicine, Cornell University, receiving a daily dose of 12 grams of CDFA per day blended in their diet for two weeks prior to challenge, and a daily dose of 6 grams thereafter. A group of five (5) animals from the same herd were fed a control diet lacking CDFA. Example 1 demonstrated that inclusion of CDFA in the diet resulted in substantial phenotypic changes in lymphocytes found in the blood and milk, including a significant increase in the expression of CD11b positive receptors on blood lymphocytes after challenge, in comparison to the findings in animals fed the same diet but without CDFA.

Example 2 examined the effect of the dose of CDFA on the expression of CD11b positive receptors on blood lymphocytes following intra-mammary challenge with *Staphylococcus aureus*. In Example 2, groups of three (3) animals derived from herds in the Ithaca, N.Y., area received a daily dose of 1.2, 6, 12 or 60 grams per day blended in their diet for two weeks prior to challenge, and daily doses of 0.6, 3, 6 or 30 grams per day, respectively, thereafter. A group of three (3) similarly obtained animals was fed the same diet lacking CDFA. Example 2 demonstrated that inclusion of incremental doses of CDFA in an animal diet resulted in dose-related increases in the expression of CD11b positive receptors on blood lymphocytes after challenge.

Figure 17:
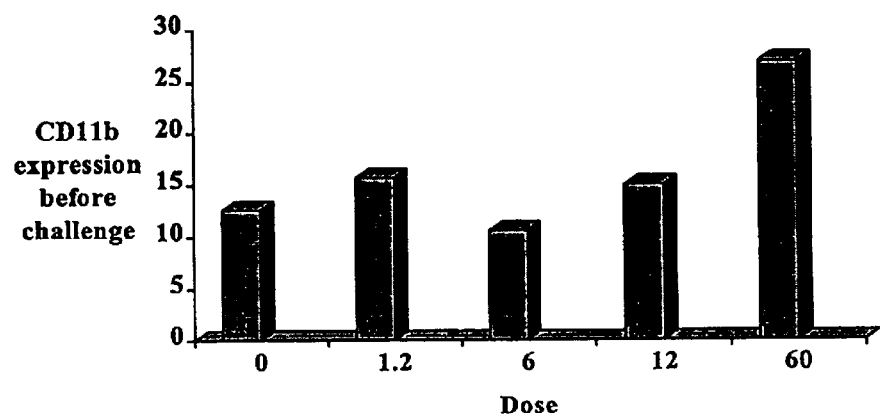
FIG. 17: Increase in CD11b percent expression on blood lymphocytes pre-inoculation of *S. aureus*.
Figure 18:
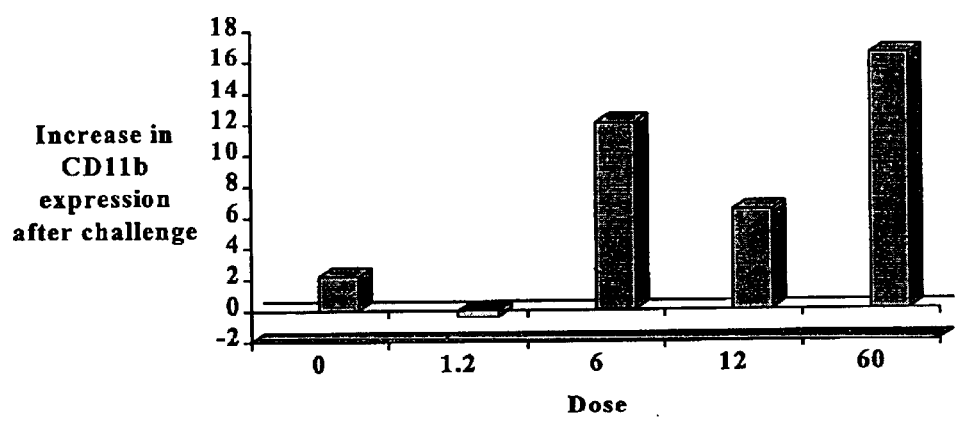
FIG. 18: Increase in CD11b percent expression on blood lymphocytes post-inoculation of *S. aureus*.
Figure 19:
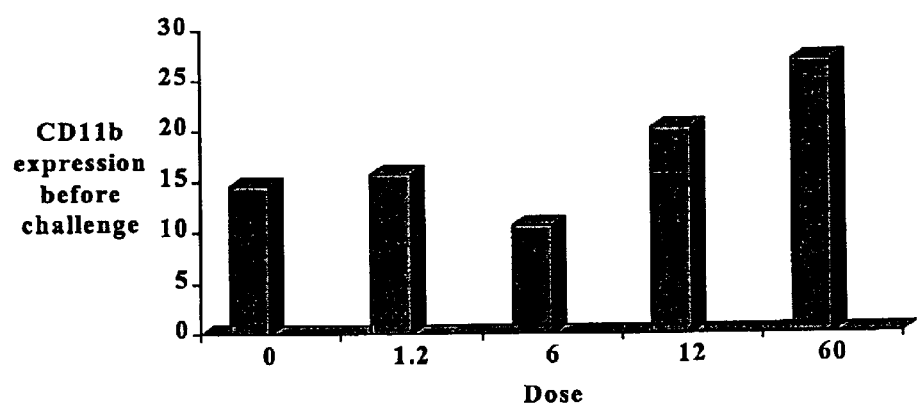
FIG. 19: Increase in CD11b percent expression on blood lymphocytes pre-inoculation of *S. aureus* (Animal No. 4723 removed).
Figure 20:
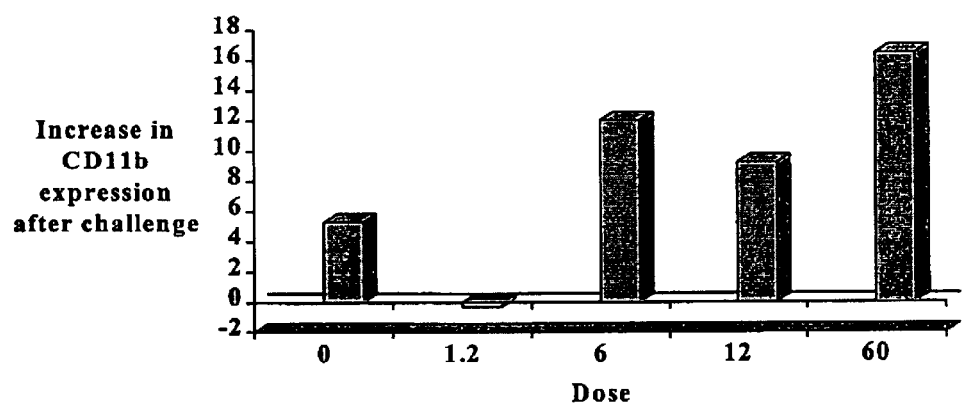
FIG. 20: Increase in CD11b percent expression on blood lymphocytes pre-inoculation of *S.aureus* (Animal No. 4723 removed).

Example 3 is provided for an analysis of the data derived in Example 1 and 2 for the purpose of statistically analyzing the overall effect of the dose of CDFA and its immuno-modulating activity. Analysis of the data indicates that the comparative change in the expression of CD11b receptors on blood lymphocytes prior to ($p=0.04$; Tables 20 & 21, FIG. 17) and after challenge increased in relation to the dose of CDFA administered ($p=0.03$; Tables 20 & 22, FIG. 18). Substantial changes occurred in the 6/3, 12/6 and 60/30 dosage groups while little or no change was seen in the control or 1.2/0.6 dosage group, indicating that a threshold exists at a dose between 1.2/0.6 and 6/3 grams per day in the diet. Again, as was shown in Example 2, the appropriate exclusion of data derived from an apparently non-responsive, outlier animal (animal No. 4723) shifted the observed dose-related response after challenge with *Staphylococcus aureus* (FIGS. 19 & 20).

The animals utilized in Example 1 were obtained from a closed herd at the College of Veterinary Medicine, Cornell University, and demonstrated very low somatic cell counts prior to treatment. In contrast, the animals utilized in Example 2 were obtained from random herds in the Ithaca, N.Y., and some animals demonstrated substantially higher somatic cell counts, although none were characterized as having clinical or sub-clinical mastitis prior to initiation of treatment. Comparison of the data derived in both studies clearly demonstrates that inclusion of CDFA in an animal diet results in an increased expression of CD11b positive receptors on blood lymphocytes following challenge regardless of the source of the animals under study. Accordingly, the immuno-modulating properties of CDFA associated with mastitis in the lactating bovine are applicable to closed as well as open, randomly-derived dairy herds and are not influenced by a level of pre-existent somatic cell counts.

TABLE 20

INCREASE IN CD11b PERCENT EXPRESSION ON BLOOD LYMPHOCYTES PRE- AND POST-INOCULATION OF *S. AUREUS*

| Dose | Study | Animal # | CD11b Pre-Chal | CD11b Post-Chal |
|---|---|---|---|---|
| 0/0 | A | 6236 | 11.80 | 9.10 |
|  |  | 6288 | 12.90 | 13.80 |
|  |  | 6273 | 11.50 | 10.50 |
|  |  | 6358 | 7.50 | 7.40 |
|  |  | 6360 | 13.00 | 18.00 |
|  | B | 6208 | 14.70 | 24.30 |
|  |  | 6262 | 10.80 | 16.10 |
|  |  | 6346 | 18.40 | 19.30 |
| 1.2/0.6 | B | 5420 | 10.70 | 8.60 |
|  |  | 6193 | 23.50 | 24.30 |
|  |  | 6487 | 12.50 | 12.50 |
| 6/3 | B | 6354 | 6.10 | 12.50 |
|  |  | 6408 | 15.00 | 39.80 |
|  |  | 6413 | 10.60 | 15.30 |
| 12/6* | A | 6301 | 13.30 | 15.50 |
|  |  | 6271 | 9.80 | 22.80 |
|  |  | 6295 | 19.70 | 29.60 |
|  |  | 6321 | 25.90 | 20.00 |
|  |  | 6378 | 1.70 | 22.30 |
|  | B | 3113 | 35.80 | 44.90 |
|  |  | 4723 | 9.60 | 2.70 |
|  |  | 5272 | 4.60 | 13.80 |
| 60/30 | B | 3267 | 24.30 | 49.00 |
|  |  | 5188 | 15.40 | 26.20 |
|  |  | 5222 | 41.00 | 54.80 |

*Statistically significantly greater post-challenge CD11b+ blood lymphocyte percentage was observed in the 12/6 gm dose group than in controls ($p = 0.03$, Mann-Whitney test).

TABLE 21

UNWEIGHTED LEAST SQUARES LINEAR REGRESSION OF DIFFERENCE IN CD11b EXPRESSION PRE-INOCULATION OF *S. AUREUS**

| PREDICTOR VARIABLES | CO-EFFICIENT | STD ERROR | STUDENT'S T | P | VIF |
|---|---|---|---|---|---|
| CONSTANT | 9.40585 | 5.64488 | 1.67 | 0.1098 |  |
| DOSE | 0.22201 | 0.09255 | 2.40 | 0.0254 | 1.1 |
| TRIAL | 1.97209 | 3.48775 | 0.57 | 0.5775 | 1.1 |
| R-SQUARED |  | 0.2486 | RESID. MEAN SQUARE (MSE) | 68.0108 |  |
| ADJUSTED R-SQUARED |  | 0.1803 | STANDARD DEVIATION | 8.24686 |  |

| SOURCE | DF | SS | MS | F | P |
|---|---|---|---|---|---|
| REGRESSION | 2 | 495.053 | 247.526 | 3.64 | 0.0431 |
| RESIDUAL | 22 | 1496.24 | 68.0108 |  |  |
| TOTAL | 24 | 1991.29 |  |  |  |

*Dose of CDFA was used as a linear regression variable. The analysis is corrected for study number (Ex. 1 vs. Ex. 2).

TABLE 22

UNWEIGHTED LEAST SQUARES LINEAR REGRESSION OF DIFFERENCE IN CD11b EXPRESSION POST-INOCULATION OF S. AUREUS*

| PREDICTOR VARIABLES | CO-EFFICIENT | STD ERROR | STUDENT'S T | P | VIF |
|---|---|---|---|---|---|
| CONSTANT | 1.83170 | 5.27452 | 0.35 | 0.7317 | |
| DOSE | 0.22353 | 0.08647 | 2.58 | 0.0169 | 1.1 |
| TRIAL | 1.01710 | 3.25892 | 0.31 | 0.7579 | 1.1 |
| R-SQUARED | | 0.2599 | RESID. MEAN SQUARE (MSE) | 59.3793 | |
| ADJUSTED R-SQUARED | | 0.1927 | STANDARD DEVIATION | 7.70579 | |

| SOURCE | DF | SS | MS | F | P |
|---|---|---|---|---|---|
| REGRESSION | 2 | 458.856 | 229.428 | 3.86 | 0.0365 |
| RESIDUAL | 22 | 1306.34 | 59.3793 | | |
| TOTAL | 24 | 1765.20 | | | |

*Dose of CDFA was used as a linear regression variable. The analysis is corrected for study number (Ex. 1 vs. Ex. 2).

EXAMPLE 4

In Vivo Assay for Evaluating Immuno-Modulatory Potentials of CDFA

An in vivo system that evaluates the expression of CD11b and phagocytosis after exposure to fluorescent beads and compares the responses of splenic leukocytes to those of peritoneal leukocytes was developed.

The studies undertaken in Example 4 were conducted to determine: 1) whether a mouse model induces local inflammation in a safe, consistent, low cost, and rapidly tested fashion; 2) whether the model provides indicators of leukocyte activation, migration, and phagocytosis; and 3) whether a colostrum-derived feed additive (CDFA) is associated with immuno-modulatory effects in a model.

Materials and Methods
Animals 12 to 16-week old Balb/c female mice (Charles River Laboratories) were fed and housed according to AAALAC guidelines (Protocol #00-09, Cornell University).

Experimental Groups

Five experiments were conducted. In the first experiment, different S. aureus concentrations, administered through intra-peritoneal injections, were tested (n=15 mice). In the second experiment, the phagocytic ability of splenic leukocytes and peritoneal leukocytes were compared (n=3). In the third experiment, treated animals received 0.1 ml of sterile CDFA sub-cutaneously (0.1 ml, twice a day for 5 consecutive days prior to testing) and groups of five mice each were tested as follows: 1) not treated with CDFA, non-inoculated with S. aureus (T−I−); 2) treated with CDFA but not inoculated (T+I−); 3) non-treated with CDFA but inoculated (T−I+); and 4) treated with CDFA and inoculated (T+I+). In the fourth experiment, two groups of four mice each were treated per os at a dose of 0.2 ml per day of a gel containing CDFA, administered intra-gastrically for five consecutive days; or 0.2 ml per day of the gel alone administered in the same fashion. All animals of the same experimental condition were euthanized and tested on the same day. In the fifth experiment, three doses were assessed. Three to five mice per dosage were treated through intra-gastric intubation, receiving 0.3 ml daily for five consecutive days of a gel containing 0%, 25% or 100% of CDFA (100%=0.2 ml).

Bacterial Inoculation

Animals were injected intra-peritoneally with 300 CFU of S. aureus ribotype 116-232-S3, a strain of bovine origin (Rivas et al., 1997) 24 hours prior to testing.

Monoclonal Antibodies and Fluorescent Beads

Fluorescein-labeled monoclonal antibodies against mouse cell surface antigens were used as follows: CD3 (for identification of lymphocytes); mouse isotype control; CD11b (for assessment of leukocyte activation); and CD14 (for identification of monocytes/macrophages). Commercially obtained fluorescent latex beads were used to assess phagocytic function.

Cell Isolation and Immunofluorescence Procedures

At the end of each experiment, mice were euthanized by cervical dislocation and the peritoneal cavity was lavaged with 6–9 ml of a solution containing 2% rabbit serum diluted in PAE buffer (PBS with 0.1% NaN2, 10% citrate, 10 mM EDTA, pH=7.2). Peritoneal leukocytes were recovered from the peritoneal lavage by centrifugation (200 g for 10 minutes). Leukocytes from each animal were then transferred to a set of five 12×75 mm polypropylene tubes, incubated first with 50 µl of a blocking buffer (10% rabbit serum in PAE, 15 minutes on ice) and later incubated with 50 µl of one of the following: 1) isotype mouse antibody (negative control), 2) anti-mouse CD3 (for identification of lymphocytes); 3) anti-mouse CD14 (for identification of macrophages); 4) anti-mouse CD11b; or 5) fluorescent beads. After 45 minutes on ice, cells were washed three times by centrifugation at 200 g and 10 minutes at 4° C. and fixed in 0.5 ml of 2% formadehyde PBS-azide. Cells were then kept in darkness at 4° C. until analyzed by flow cytometry (FACSCalibur, Becton-Dickinson, San Jose, Calif.). At least 30,000 events (cells) were acquired per condition. Flow cytometry data were acquired and analyzed with commercially available software (CELLQuest, Becton-Dickinson).

Statistical Analysis

The Mann-Whitney test for comparison of medians, confidence intervals, and correlation analysis was conducted with commercially available statistical software (Minitab 12.2, Minitab Inc., University Park, Pa.). P values <0.05 were considered to be significant.

Results

Experiment I (Bacterial Recovery)

Three S. aureus concentrations were assessed: a) $1 \times 10^3$, b) $1 \times 10^4$, and c) $1 \times 10^5$ CFU. No bacterial challenge resulted in the death of any mouse, and no bacteria were recovered in any experiment following incubation for 24 hours (data not shown).

Experiment II (Comparison between Splenic and Peritoneal Leukocyte Phenotypes)

Two splenic subpopulations were observed for both macrophages and PMNs. In both cell types, the predominant subpopulation was composed of lower phagocytic cells (LPC). The LPC subset represented 82.3% or more of all macrophages. In PMN, the percentage of higher phagocytic cells (HPC) was higher (12.6% or more), but still significantly less than that of LPC.

A significant difference was observed in PMN of peritoneal phagocytes from the same animals. The HPC subpopulation was predominant, representing 69.1% or more of all PMN. Peritoneal macrophages, while showing a greater percentage of HPC than splenic macrophages (1.4% or higher), were still significantly less than LPC (52.8% or greater, n=3 mice, Table 23). Thus, a selective migration of HPC PMN from tissue to the inflammatory site was observed. Since the phagocytic profile of splenic phagocytes was unrelated to that of peritoneal cells, further studies only utilized peritoneal phagocytes.

cell can phagocytize between 100 times and 1,000 times more than a "M4" cell.

TABLE 23

COMPARISON OF SUBPOPULATIONS OF DIFFERENT PHAGOCYTIC ABILITY BETWEEN SPLENIC VS. PERITONEAL PHAGOCYTES

| Mouse | Splenic LPC MØ % | Splenic HPC MØ % | Splenic LPC PMN % | Splenic HPC PMN % | Peritoneal LPC MØ % | Peritoneal HPC MØ % | Peritoneal LPC PMN % | Peritoneal HPC PMN % |
|---|---|---|---|---|---|---|---|---|
| A | 83.9 | 1.0 | 81.5 | 17.1 | 52.8 | 4.1 | 20.1 | 74.9 |
| B | 82.3 | 1.0 | 84.8 | 14.3 | 88.0 | 4.6 | 29.2 | 69.1 |
| C | 83.1 | 1.0 | 87.1 | 12.6 | 54.6 | 1.4 | 19.3 | 80.2 |

Figure 21A:
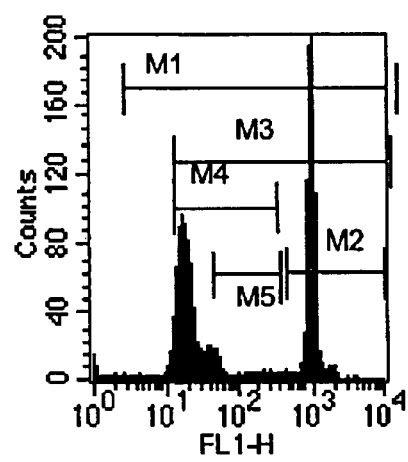
FIG. 21: Median (log) fluorescence intensity (FL1-H) of peritoneal macrophages (A) and PMN (B) after exposure to fluorescent beads in a representative non-treated, non-inoculated animal. Cells under gate M3 include >95% of all cells of each type. At least two major sub-populations are identified: 1) cells of less phagocytic ability (under region M4); and 2) cells of greater phagocytic ability (under region M2).
Figure 21B:
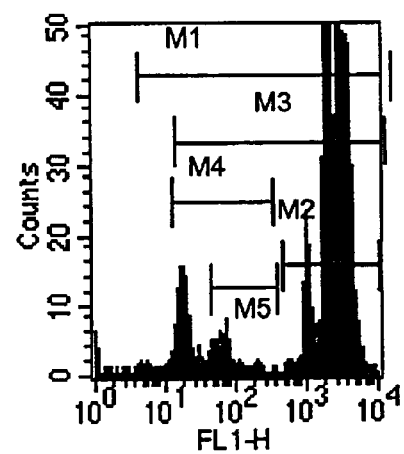

Percentage of low phagocytic cells (LPC) and high phagocytic cells (HPC) as a percentage of all macrophages (MØ) or polymorphonuclear cells (PMN), respectively Experiment III (Sub-Cutaneous Administration, Peritoneal Leukocytes)
Phagocyte Sub-Populations Distinct sub-populations were observed both in macrophages and PMN that differed in ability to phagocytize fluorescent beads. As indicated in FIG. 21, at least two major subpopulations (and up to five minor sub-populations) were identified based on their median fluorescence intensity after incubation with fluorescent beads. This phagocytic profile-based identification provided another way to differentiate macrophages from PMN. Most macrophages belong to the less-phagocytic subset (M4) whereas most PMN belong to the more phagocytic subset (M2). More sub-populations can be visualized (i.e., subset M5 of the low phagocytic macrophage and PMN subpopulations; and at least three peaks in the PMN "M2" subpopulation, suggest additional functional differences in each of these cell types). The sum of "Reg4" and "Reg2" was between 91 and 99% of all gated cells, regardless of phagocyte type and treatment, demonstrating that increases in one sub-population implied decreases in the other cell type. The difference in median phagocytosis per cell is up to 2 orders of magnitude when comparing less and more phagocytic macrophages, and up to 3 orders of magnitude when comparing less and more phagocytic PMN, demonstrating that, on average, a "M2"

In addition to scatter-based and monoclonal-based identifications, the phagocytic profile distinguished unequivocally the macrophage profile from that of PMN. Macrophages were characterized by a larger proportion of cells of lower phagocytic ability (Region 4 cells), and a single subpopulation of higher phagocytic ability (characterized by a single peak in Region 2), resulting in a median HPC/LPC ratio of 0.62 (n=5, Table 24). In contrast, PMN showed a higher proportion of high phagocytic cells (Region 2 cells) than that of lower phagocytic ability (Region 4 cells) and showed several subsets within the higher phagocytic subgroup (expressed as several peaks within the Region 2 cells), which resulted in a median HPC/LPC ratio of 11.21 (n=5, Table 24).

Data from the non-treated group of mice (T–) showed that the relative proportions of these subpopulations between macrophages and PMN differed after *S. aureus* challenge. While LPC increased marginally, although significantly, post-challenge (Region 4 cells increasing from a group median of 57.7% to 67.5%), the percentage of LPC PMN increased from 7.7% to 14.6% (Tables 24 & 25).

TABLE 24

OVERVIEW OF VALUES OBTAINED FOLLOWING SUBCUTANEOUS ADMINISTRATION OF CDFA

| Variable Experimental group, animal | TII | MØ CD11b (% of total cells) | PMN CD11b (% of total cells) | MØ CD11b % | PMN CD11b % | LPC MØ (% of gated MØ) | HPC MØ (% of gated MØ) | LPC PMN (% of gated PMN) | HPC PMN (% of gated PMN) | HPC MØ (as % of all cells) | LPC MØ (as % of all cells) | MØ HPC/ LPC ratio | HPC PMN (as % of all cells) | LPC PMN (as % of all cells) | PMN HPC/ LPC ratio |
|---|---|---|---|---|---|---|---|---|---|---|---|---|---|---|---|
| T – I– | | | | | | | | | | | | | | | |
| A | 0.70 | 1.73 | 3.75 | 9.20 | 77.22 | 51.9 | 36.1 | 7.9 | 89.0 | 3.21 | 5.18 | 0.62 | 8.72 | 0.89 | 9.80 |
| B | 0.82 | 1.93 | 1.35 | 7.15 | 39.74 | 54.8 | 40.7 | 7.7 | 91.5 | 3.29 | 4.67 | 0.70 | 11.55 | 1.03 | 11.21 |
| C | 0.51 | 0.69 | 1.35 | 3.57 | 52.05 | 61.7 | 27.5 | 4.7 | 91.9 | 2.37 | 5.52 | 0.43 | 8.08 | 0.42 | 19.24 |
| D | 1.10 | 2.48 | 1.27 | 10.94 | 40.38 | 57.7 | 36.8 | 8.3 | 91.1 | 2.47 | 3.99 | 0.62 | 10.63 | 0.99 | 10.74 |
| E | 1.02 | 2.53 | 1.42 | 8.52 | 52.62 | 60.2 | 38.6 | 5.8 | 94.0 | 3.06 | 4.72 | 0.65 | 11.47 | 0.71 | 16.15 |
| T + I– | | | | | | | | | | | | | | | |
| A | 1.11 | 0.86 | 2.80 | 3.35 | 81.27 | 58.8 | 37.4 | 2.3 | 97.0 | 3.09 | 4.58 | 0.67 | 13.92 | 0.30 | 46.40 |
| B | 0.85 | 1.75 | 1.59 | 6.18 | 76.32 | 50.1 | 42.0 | 1.9 | 97.6 | 4.05 | 4.79 | 0.85 | 15.01 | 0.30 | 50.03 |
| C | 0.51 | 1.92 | 0.57 | 9.03 | 40.64 | 49.4 | 47.1 | 2.8 | 96.6 | 3.64 | 3.78 | 0.96 | 15.38 | 0.43 | 35.77 |
| D | 1.10 | 1.36 | 1.62 | 4.22 | 72.78 | 49.1 | 40.5 | 2.3 | 96.9 | 4.55 | 6.12 | 0.74 | 14.66 | 0.41 | 35.76 |
| E | 0.58 | 1.76 | 1.04 | 7.55 | 60.98 | 43.6 | 47.1 | 1.4 | 97.8 | 3.53 | 3.35 | 1.05 | 13.09 | 0.19 | 68.89 |

TABLE 24-continued

OVERVIEW OF VALUES OBTAINED FOLLOWING SUBCUTANEOUS ADMINISTRATION OF CDFA

| Variable Experimental group, animal | TII | MØ CD11b (% of total cells) | PMN CD11b (% of total cells) | MØ CD11b % | PMN CD11b % | LPC MØ (% of gated MØ) | HPC MØ (% of gated MØ) | LPC PMN (% of gated PMN) | HPC PMN (% of gated PMN) | HPC MØ (as % of all cells) | LPC MØ (as % of all cells) | MØ HPC/ LPC ratio | HPC PMN (as % of all cells) | LPC PMN (as % of all cells) | PMN HPC/ LPC ratio |
|---|---|---|---|---|---|---|---|---|---|---|---|---|---|---|---|
| T − I+ | | | | | | | | | | | | | | | |
| A | 2.17 | 9.05 | 2.94 | 21.63 | 37.08 | 78.0 | 20.1 | 27.1 | 72.2 | 3.58 | 13.93 | 0.26 | 12.92 | 4.84 | 2.67 |
| B | 2.12 | 10.30 | 4.02 | 26.58 | 52.62 | 76.4 | 20.8 | 21.4 | 77.6 | 3.24 | 11.94 | 0.27 | 11.82 | 3.28 | 3.60 |
| C | 0.97 | 2.30 | 1.36 | 7.77 | 50.29 | 55.8 | 43.4 | 9.1 | 90.9 | 2.98 | 3.71 | 0.80 | 11.53 | 1.13 | 10.20 |
| D | 1.35 | 5.43 | 2.94 | 16.91 | 56.49 | 67.5 | 31.7 | 14.0 | 85.6 | 4.43 | 9.11 | 0.49 | 11.99 | 1.86 | 6.45 |
| E | 1.14 | 3.33 | 1.50 | 14.43 | 47.42 | 65.0 | 33.8 | 14.6 | 84.1 | 4.10 | 7.13 | 0.57 | 9.70 | 1.51 | 6.42 |
| T + I+ | | | | | | | | | | | | | | | |
| A | 1.56 | 5.78 | 3.98 | 17.92 | 79.69 | 54.5 | 40.0 | 6.5 | 92.4 | 5.92 | 8.25 | 0.72 | 14.14 | 1.03 | 13.73 |
| B | 3.19 | 10.35 | 3.45 | 23.47 | 68.57 | 65.9 | 30.2 | 9.8 | 89.8 | 5.10 | 11.28 | 0.45 | 14.17 | 1.56 | 9.08 |
| C | 4.12 | 19.92 | 4.32 | 42.65 | 72.49 | 74.6 | 21.7 | 8.6 | 91.1 | 4.54 | 15.75 | 0.29 | 14.03 | 1.34 | 10.47 |
| D | 1.59 | 6.10 | 1.50 | 17.67 | 50.00 | 59.4 | 33.9 | 9.5 | 89.6 | 4.86 | 8.80 | 0.55 | 12.26 | 1.33 | 9.22 |
| E | 1.66 | 1.96 | 3.84 | 5.92 | 85.92 | 46.8 | 44.5 | 3.9 | 95.6 | 5.58 | 6.22 | 0.90 | 15.38 | 4.19 | 3.67 |

T − I−: not-treated, not inoculated with S. aureus;
T + I− treated with CDFA, not inoculated;
T − I+, not treated, inoculated with S. aureus;
T + I+ treated with CDFA and inoculated with S. aureus

TABLE 25

SUMMARY OF RESULTS FOLLOWING SUBCUTANEOUS ADMINISTRATION OF CDFA

| Experimental Group Variable | T−I− | T+I− | T−I+ | T+I+ |
|---|---|---|---|---|
| TII | 0.82 | 0.85 | 1.35[A] | 1.66 |
| MØ CD11b % | 8.52 | 6.18 | 16.91[A] | 17.92 |
| PMN CD11b % | 52.05 | 72.78[B] | 50.29 | 72.49 |
| MØ CD11b % (% of total cells) | 1.93 | 1.75 | 5.43[A] | 6.10 |
| PMN CD11b % (% of total cells) | 1.35 | 1.59 | 2.94[A] | 3.84 |
| LPC MØ as MØ % | 57.70 | 49.4 | 67.5[A] | 59.4 |
| HPC MØ as MØ % | 36.80 | 42.0[B] | 31.7 | 33.9 |
| LPC PMN as PMN % | 7.70 | 2.3 | 14.6[A] | 8.6 |
| HPC PMN as PMN % | 91.50 | 97.0[B] | 84.1 | 91.1[B] |
| HPC MØ (as % of all cells) | 3.06 | 3.64[B] | 3.58 | 5.10[B] |
| LPC MØ (as % of all cells) | 4.72 | 4.58 | 9.11[A] | 8.80 |
| MØ HPC/LPC Ratio | 0.62 | 0.85[B] | 0.49 | 0.55 |
| HPC PMN (as % of all cells) | 10.63 | 14.66[B] | 11.82 | 14.14[B] |
| LPC PMN (as % of all cells) | 0.89 | 0.30 | 1.86[A] | 1.34 |
| PMN HPC/LPC ratio | 11.21 | 46.40[B] | 6.42 | 9.22 |
| Overall MØ MFI | 35 | 50[B] | 32 | 42 |
| Overall PMN MFI | 2091 | 1894 | 1778 | 1827 |
| MØ HPC MFI | 843 | 850 | 881 | 905[B] |
| PMN HPC MFI | 2247 | 1911 | 1999 | 1860 |

T−I−: not-treated, not inoculated with S. aureus,
T+I−: treated with CDFA, not inoculated,
T−I+, not treated, inoculated,
T+I+: treated and inoculated
Median values per group (n = 5)
LPC: Low phagocytic cells (or "Region 4" cells).
HPC: High phagocytic cells (or "Region 2" cells)
A: statistically significant change associated with S. aureus challenge ($P < 0.05$, Mann-Whitney test)
B: statistically significant change associated with treatment ($P < 0.05$, Mann-Whitney test)

Peritoneal Leukocyte Counts

The control group (T–I–) showed a greater proportion of lymphocytes than that of phagocytes (macrophages and polymorphonuclear cells) as indicated by a 0.82 median inflammatory response. This is indicated as the ratio between phagocytes/lymphocytes or Total Inflammatory Index (TII). Mice treated, but not inoculated, with S. aureus (T+I–), also displayed a TII of less than one, which demonstrates that treatment does not elicit a per se inflammatory response. In contrast, both S. aureus-inoculated groups (T–I+ and T+I+) showed a TII above 1 (1.35 and 1.66, respectively, Tables 24 & 25), indicating that phagocytes had increased and/or lymphocytes had decreased after bacterial challenge, which demonstrates that the assay induced an acute inflammatory response.

CD11b Expression as a Percentage of All Cells

Figure 22:
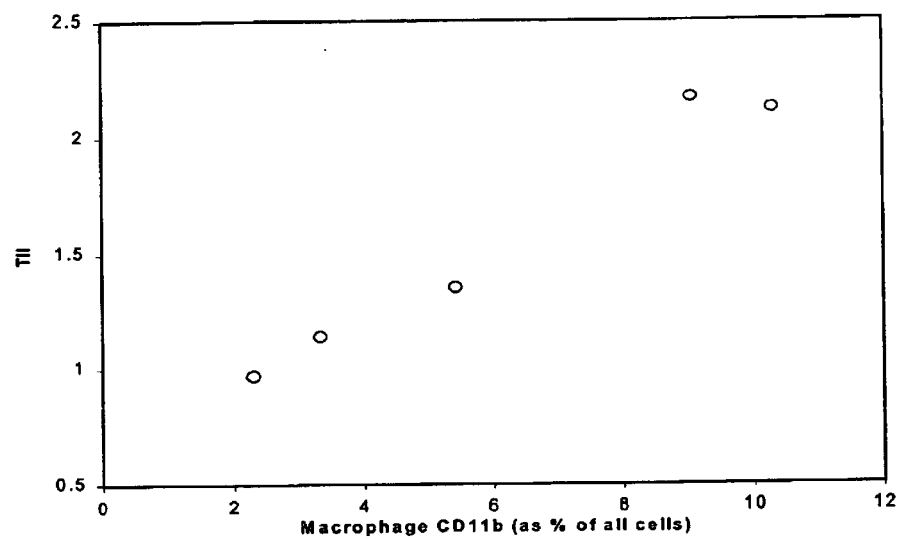
FIG. 22: Correlation between macrophage CD11b expression (percent of macrophage CD11b+ cells among all cells) and inflammatory response (expressed by the ratio between all phagocyte/lymphocyte counts, or TII) in non-treated, inoculated (T–I+) animals (n=5, r=0.983, P<0.003).

Expressed as a percentage of the total number of cells (i.e., lymphocytes, macrophages and PMN), CD11b positive macrophages and PMN increased significantly after inoculation. A highly significant positive correlation was observed between TII and the percent of CD11b positive macrophages (expressed as a percentage of total cells), a correlation indicating that 98% of the variation in the magnitude of the inflammatory response (TII) was explained by CD11b positive macrophages (FIG. 22). The expression of CD11b positive PMN (as a percent of all cells) was also associated with the TII, although it did not reach statistical significance ($r=0.85$, $P=0.069$, $n=5$). Thus, measurement of the CD11b receptor on macrophages as described is an accurate predictor of the inflammatory response.

Expression of CD11b on Peritoneal Phagocytes

Figure 23:
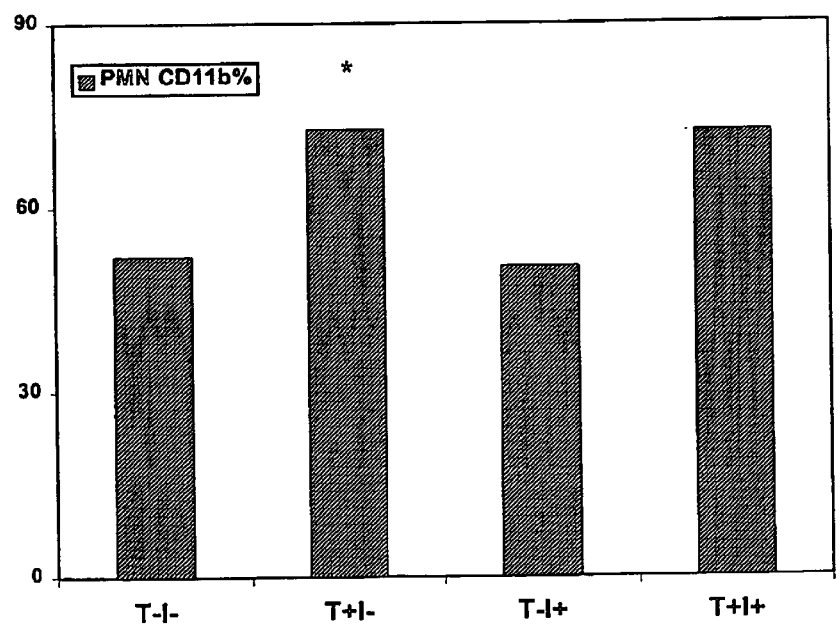
FIG. 23: Median percentage of peritoneal CD11b+ PMN (n=5). The T+I– group showed a greater median percentage of CD11b+ PMN than that of T–I– animals (P<0.03).

Mice inoculated with S. aureus showed statistically significant greater percentages of CD11b positive macrophages (median=16.91) than non-inoculated animals (median=8.52, Tables 24 & 25). In contrast, the expression of CD11b on PMN, but not on macrophages, increased significantly in T+I– over T–I– mice ($P<0.05$). Expression of CD11b on PMN was also greater in T+I+ when compared to T–I+, although the magnitude did not reach statistical significance ($P=0.10$). This observation indicates that treatment with CDFA induced an effect demonstrable as a greater expression of activated PMN (FIG. 23).

Low Phagocytic Macrophages (LPC MØ) as Percentage of All Macrophages

Treatment with CDFA was associated with a significantly lower (P<0.05) proportion of low phagocytic macrophages in both treated groups (T+I−<T−I, and T+I+<T−I+, Tables 24 & 25).

High Phagocytic Macrophages (HPC MØ) as Percentage of All Macrophages

In contrast the LPC MØ observation, treatment with CDFA was associated with a significant increase in the proportion of high phagocytic macrophages (P<0.05) in both treated groups (T+I−>T−I−, and T+I+>T−I+, Tables 24 & 25).

Low Phagocytic Polymorphonuclear Cells (LPC PMN) as Percentage of All PMN

Figure 24:
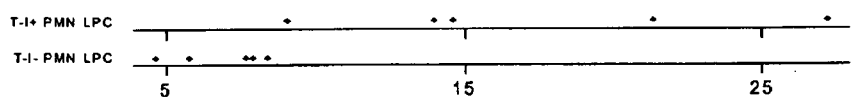
FIG. 24: Dot plot distribution of values for groups T–I– and T–I+.

The proportion of LPC PMN was significantly lower (P<0.001) in T+I−, and in T+I+, compared to T−I+ (P=0.02, Tables 24 & 25). Values from the T−I− and T−I+ groups did not overlap (FIG. 24).

High Phagocytic Polymorphonuclear Cells (HPC PMN) as a Percentage of All PMN

In contrast to the LPC PMN observation, the proportion of highly phagocytic PMN was greater in T+I− than in T−I− (P<0.0001), and greater in T+I+ (median %=91.1) compared to T−I+ (median %=84.1; P=0.02, Tables 24 & 25).

Macrophage Sub-Population of Greater Phagocytic Ability (High Phagocytic Cells or HPC) as a Percent of Total Cells Significant differences were found in the proportion of the macrophage sub-set of greater phagocytic ability ("M2" or HPC). Both treated groups showed a significantly greater percentage of macrophages under gate M2 than non-treated groups (Tables 24 & 25).

Macrophage Sub-Population of Less Phagocytic Ability (Low Phagocytic Cells or LPC) as a Percent of Total Cells In contrast to the observation with respect to HPC, S. aureus challenge was associated with a 2-fold increase in the macrophage sub-set of less phagocytic ability, while treatment was not (Tables 24 & 25). Treatment with CDFA was also associated with a relative decrease (although not significant) of "Region 4" macrophages (LPC). This finding may explain why CDFA treatment induced more "Region 2" macrophages without significantly increasing the overall percentage of CD11b+ macrophages. A selective recruitment of more phagocytic macrophages seemed to be compensated with a lower percentage of less phagocytic cells, which resulted in an overall similar number of CD11b positive macrophages in treated and non-treated animals.

Ratio Between More Phagocytic/Less Phagocytic Macrophages (HPC/LPC) as a Percent of Total Cells To determine a single measurement that captures the overall relationship between HPC and LPC cell sub-sets, a ratio was created that compared the relationship between more phagocytic and less phagocytic macrophages (HPC/LPC ratio). The HPC/LPC index indicated that non-treated animals displayed a lower HPC/LPC ratio after inoculation, whereas T+I− animals had a significantly higher index than T−I− mice (Tables 24 & 25).

PMN of Greater Phagocytic Ability (High Phagocytic Cells or HPC) as a Percent of Total Cells A statistically significant increase (38%) in PMNs of greater phagocytic ability (those that can phagocytize 100 to 1,000 times more fluorescent beads per cell) was observed in T+I− (14.66%) than in controls (10.63%). This observation leads to a conclusion that CDFA treatment was associated with an increase in phagocytic ability per cell between 38 (38% of 100) and 380 (38% of 1,000) times greater than the average ability of non-treated PMNs. Similarly, a significant 20% increase was observed in T+I+ (14.14%) when compared to T−I+ animals (11.82%) in the same cell sub-set (Tables 24 & 25).

PMN of Less Phagocytic Ability (Low Phagocytic Cells or LPC) as a Percent of Total Cells In contrast to the observation of PMN HPC, treated animals showed a 2-fold lower percent of "M4" PMN compared to T−I− animals. After inoculation, non-treated animals displayed a 2-fold higher percent in LPC PMN compared to non-inoculated animals and also a 39% greater increase than that seen in the T+I+ group. This finding indicates a response less capable of phagocytizing beads in non-treated animals in comparison to CDFA treated animals (Tables 24 & 25).

Ratio Between More Phagocytic/Less Phagocytic PMN as a Percent of Total Cells

A highly significant 4-fold greater PMN HPC/LPC index was observed in T+I− when compared to T−I− animals. This finding is attributable to both greater HPC and lower LPC percentages displayed by T+I− animals when compared to T−I− animals. Additionally, a 44% greater phagocytic index (although not reaching statistical significance) was found after inoculation in T+I+ animals, when compared to that observed in T−I+ animals (Tables 24 & 25).

Overall Phagocytic Ability

Regardless of the cell subpopulation, the overall ("Region 3") median fluorescence intensity (MFI) was increased in macrophages in the T+I− group in comparison to that found in T−I− mice (P<0.007), but the same response was not observed with PMNs (Table 26).

TABLE 26

OVERALL PHAGOCYTIC ABILITY ("REGION 3" CELLS) FOLLOWING SUBCUTANEOUS ADMINISTRATION OF CDFA

| Variable Experimental Group, Animal | Overall MØ MFI | Overall PMN MFI | HPC MØ MFI | HPC PMN MFI |
|---|---|---|---|---|
| T−I−, | | | | |
| A | 37 | 2017 | 865 | 2227 |
| B | 37 | 2187 | 850 | 2287 |
| C | 18 | 1827 | 842 | 1911 |
| D | 30 | 2091 | 835 | 2247 |
| E | 35 | 2227 | 835 | 2288 |
| T+I−, | | | | |
| A | 43 | 1946 | 889 | 1999 |
| B | 50 | 1877 | 873 | 1911 |
| C | 103 | 2110 | 850 | 2167 |
| D | 39 | 1811 | 842 | 1843 |
| E | 577 | 1894 | 842 | 1911 |
| T−I+, | | | | |
| A | 32 | 1731 | 881 | 1999 |
| B | 32 | 1778 | 889 | 2017 |
| C | 65 | 1911 | 881 | 2167 |
| D | 34 | 1778 | 881 | 1877 |
| E | 29 | 1762 | 873 | 1843 |
| T+I+, | | | | |
| A | 48 | 1827 | 905 | 1860 |
| B | 42 | 1778 | 913 | 1827 |
| C | 34 | 1763 | 913 | 1794 |

TABLE 26-continued

OVERALL PHAGOCYTIC ABILITY ("REGION 3" CELLS) FOLLOWING SUBCUTANEOUS ADMINISTRATION OF CDFA

| Variable Experimental Group, Animal | Overall MØ MFI | Overall PMN MFI | HPC MØ MFI | HPC PMN MFI |
|---|---|---|---|---|
| D | 33 | 1843 | 897 | 1911 |
| E | 286 | 1894 | 889 | 1946 |

T−I−: not-treated, not inoculated with S. aureus;
T+I−: treated with CDFA, not inoculated;
T−I+, not treated, inoculated with S. aureus;
T+I+: treated with CDFA and inoculated with S. aureus.

Summary of Experiment III (Sub-Cutaneous Administration of CDFA)

This investigation showed several indications of an effect of bacterial insult on inflammation based upon a greater TII, greater percentage of CD11b positive macrophages and CD11b positive PMN (when expressed as percent of all cells) in T−I+ than in T−I− animals. Accordingly, this finding demonstrates an association between increased expression of CD11b (the early indication of leukocyte activation required to initiate cell adhesion and transendothelial migration processes), and the magnitude of the inflammatory response (expressed as the phagocyte/lymphocyte counts ratio, or TII). In addition, inflammation is also indicated by a greater percentage of cells of less phagocytic ability (both macrophages and PMN), as expressed by the LPC ("Region 4") value of each cell type.

Figure 25:
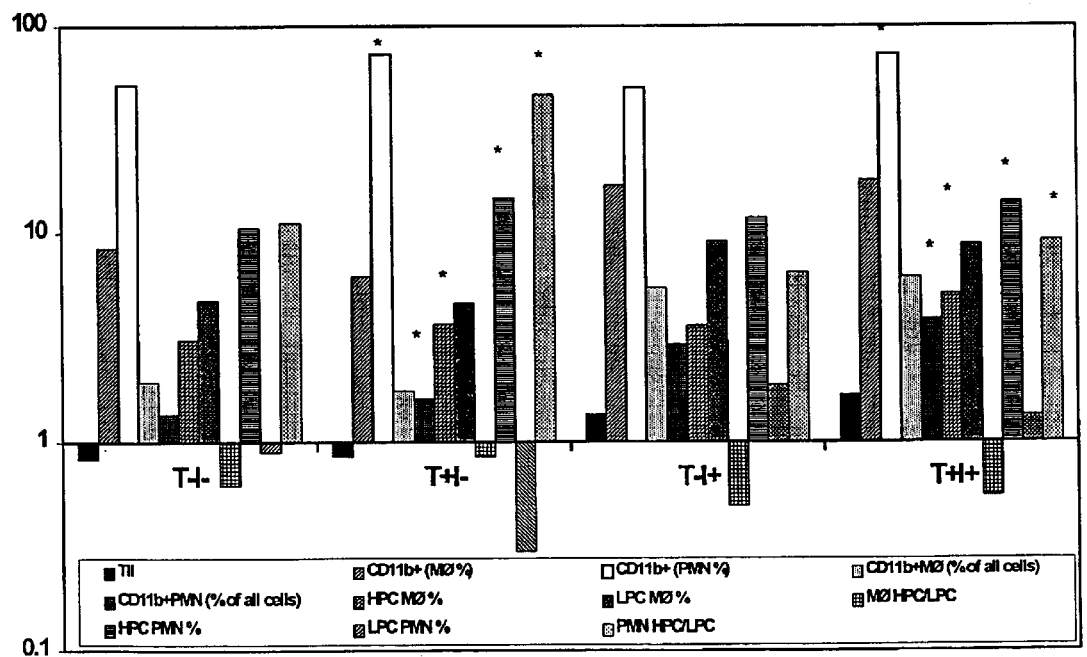
FIG. 25: Summary of results from Example 4. Median results per group (n=5). Asterisk indicates a significant difference between one or both groups treated with CDDS versus T–I– and/or T–I+ animals (P<0.05).

Treatment with CDFA is associated with significantly higher percentages of CD11b positive PMN, an increased HPC macrophage percentage, and an increased HPC PMN percentage, resulting in an overall increase in phagocytic capability (Table 24 and FIG. 25).

Experiment IV (Oral Administration of CDFA)

Treatment was associated with a selective involvement of PMN of greater phagocytic ability (HPC), demonstrated by two lines of independent observations: a) the PMN HPC/LPC ratio, as a percentage of all cells, was 2.5 times greater in treated than in control animals; and b) the median fluorescence intensity (MFI) was greater for HPC PMN, which also resulted in an overall greater MFI for all PMN, regardless of the cell sub-population being considered. In other words, the present study demonstrates that when compared to the control animals, there were 2.51 times (7.16/2.85) more high phagocytic PMN in treated animals, the cell sub-population showing 100 to 1000 times greater phagocytic function than LPC PMN. In addition, the average HPC cell showed 6% (2572/2426) greater phagocytic function in treated animals than the average HPC PMN in control animals. This observation represents a 32% (2396/1811) greater phagocytic function in all PMN regardless of sub-population in treated animals when compared to control animals (Tables 27 & 28).

TABLE 27

OVERVIEW OF VALUES OBTAINED FOLLOWING ORAL ADMINISTRATION OF CDFA

| Variable Experimental Group Animal | Overall MØ MFI | HPC MØ MFI | Overall PMN MFI | HPC PMN MFI | PMN HPC/LPC ratio (% all cells) | PMN HPC/LPC ratio (% of gated PMN) |
|---|---|---|---|---|---|---|
| T−, | | | | | | |
| A | 15.26 | 882 | 2350 | 2525 | 5.25 | 5.2 |
| B | 11.97 | 882 | 1811 | 2350 | 3.50 | 3.5 |
| C | 22.67 | 898 | 1568 | 1877 | 1.53 | 1.5 |
| D | 21.48 | 898 | 1811 | 2503 | 2.20 | 2.2 |
| T+, | | | | | | |
| A | 27.60 | 922 | 2288 | 2548 | 6.78 | 6.8 |
| B | 18.43 | 882 | 2996 | 3308 | 7.55 | 7.5 |
| C | 23.29 | 906 | 2503 | 2595 | 8.90 | 8.9 |
| D | 20.54 | 914 | 2187 | 2525 | 5.01 | 5.0 |

T−: not-treated,
T+: treated with CDFA

TABLE 28

SUMMARY OF RESULTS FOLLOWING ORAL ADMINISTRATION OF CDFA

| Variable Group (n = 4, median) | CD11b + PMN % (% of total cells) | MØ HPC/LPC Ratio (% all cells) | PMN HPC/LPC Ratio (% all cells) | MFI of HPC MØ | MFI of HPC PMN | Overall MØ MFI | Overall PMN MFI |
|---|---|---|---|---|---|---|---|
| T− | 56.5 | 0.18 | 2.85 | 890 | 2426 | 18.4 | 1811 |
| T+ | 72.1 | 0.30 | ..7.16[A] | 910 | ..2572[A] | 21.9 | ..2396[A] |

T−: not-treated (placebo treatment); T+: treated with CDFA.
LPC: Low phagocytic cells (or "Region 4" cells).
HPC: High phagocytic cells (or "Region 2" cells)
[A]statistically significant change associated with treatment ($P < 0.05$, Mann-Whitney test)

Experiment V (Assessment of Dose-Related Responses, Intra-Gastric Administration)

CDFA treatment evoked responses consistent with a dose-dependent relationship. Significantly greater percentages of high phagocytic ("Region 2") PMN were observed in treated (100%) than in control animals (Table 29). The number of high phagocytic PMN per low phagocytic PMN varied from 13.9 in controls, to 25 HP PMN per LP PMN in animals treated with 25% of a 0.2 ml dose, and to 33 HP cells per LP cell at a 100% dose (Table 29). Since, on average, each HP granulocyte has a phagocytic ability 100 to 1000 times greater than low phagocytic cells, this represents 1.8 HP cells per LP cell (25/13.9) or 180 to 1800 times greater PMN-dependent phagocytic ability with the 25% dose, and 2.37 HP cells per LP cell (33/13.9) or 237 to 2370 greater phagocytic ability with the 100% dose.

TABLE 29

ASSESSMENT OF DOSE-RELATED RESPONSES IN INTRAGASTRIC-TREATED MICE

| Variable Animal | HP PMN (0% dose) | HP PMN (25% dose) | HP PMN (100% dose)* | HP/LP PMN (0% dose) | HP/LP PMN (25% dose) | HP/LP PMN (100% dose)* |
|---|---|---|---|---|---|---|
| A | 13.4783 | 25.0992 | 37.8988 | 93.00 | 96.13 | 97.40 |
| B | 13.9254 | 12.0078 | 23.8139 | 93.30 | 92.10 | 95.97 |
| C | Nt | 18.9619 | 55.1798 | Nt | 94.62 | 98.22 |
| D | 17.9753 | 36.8788 | 20.5996 | 94.73 | 97.36 | 95.17 |
| E | Nt | 30.7238 | 33.0683 | Nt | 96.78 | 96.89 |

HP: High phagocytic ("Region 2") PMN
LP: Low phagocytic ("Region 4") PMNHP/LP
PMN: Median number of HP PMN per LP PMN
*: statistically greater than Control (0% dose, p < 0.03).

Discussion

The findings expressed herein describe a rather benign assay, as indicated by an observed lack of bacterial recovery in a broad range of bacterial concentrations. In addition, the findings are repeatable, as suggested by the low variation in the percentage of LPC PMN of T–I–, showing an upper limit (8.69, at 94% confidence) lower than the lower limit of the T–I+ interval (9.05, FIG. 24). Accordingly, the assay provided non-overlapping indicators for controls (T–I–) and inflamed (T–I+) animals.

The assay described in Example 4 was designed to measure local inflammation, but not infection, differentiating the assay from those that include the compounded effects of infection in addition to those of inflammation. By virtue of using a viable bacterial inoculum, it is postulated that the model as described more closely mimics an in vivo inflammatory challenge than assays such as those based on thioglycollate injections (Ábel et al., 1991; Bogen et al., 1994). In vitro assays may not have the capability to model all relevant variables of complex inflammatory processes (Schnitzler et al., 1998). For example, cell lines, apart from their proliferation, often lack specialized macrophage molecules (McKnight and Gordon, 1998). On the other hand, in vitro systems do not necessarily investigate the cells specifically relevant to the site of interest (i.e., those found at the inflammatory site). In contrast, the in vivo assay described herein demonstrated the contrast existing between the phagocytic profile of spleen cells vs. peritoneal cells. While in vitro assays appear to be rather straightforward, the reported assay is also uncomplicated and rapid. Only one day is required to induce inflammation and the results of testing at least six (6) animals can be obtained in the same testing day. The results confirm that the rodent model is a suitable one for bovine mastitis in the sense that it evaluates local (peritoneal) leukocytes elicited in response to a local infusion of a viable (but not infective) S. aureus strain of bovine origin.

Various mouse phagocytic subpopulations of peritoneal macrophages have been previously reported (Plasman and Vray, 1994). Consistent with those studies, two major functionally different subpopulations were observed. Furthermore, a subset within the macrophage subpopulation of lower phagocytic ability was found (identified as "Region 5" cells) and reported for the first time.

The studies included in Example 4 also demonstrate that peritoneal PMN include at least two functional subpopulations, and perhaps as many as five such subpopulations, which cannot be identified by scatter light-based or monoclonal antibody-based procedures, but can be identified by exposure to fluorescent beads. Thus, the assay described provides a new means to expand the armamentarium of tools available for functional evaluations of peritoneal phagocytes.

Increased expression of CD11b on peritoneal PMN after a 24-hour induction of peritonitis in association with enhanced phagocytic function has been reported previously (Zhang et al., 1998). Increased CD11b expression on mouse neutrophils is required to phagocytize S. aureus (Schnitzler et al., 1999).

It therefore follows that the subject colostrum-derived feed additive CDFA is associated with immuno-modulatory effects that may be relevant in protective responses against S. aureus. Enhanced leukocyte activation, as expressed by CD11b, was observed in PMN, as well as selective recruitment of HPC, both in macrophages and PMN, which expanded significantly the median phagocytic ability per cell. Thus, the findings described complement the findings in Examples 1, 2, and 3 in which the colostrum-derived feed additive was used to treat lactating cows where the mammary glands were challenged with the same bacterial pathogen.

In animals treated orally, significantly increased median fluorescence intensity per PMN was observed in the subset of greater phagocytic function. This observation suggests that low pH (i.e., gastric fluids) does not inactivate the immuno-modulatory activity associated with the colostrum derivative (CDFA). This finding is consistent with other reports which have demonstrated that milk constituents are associated with increased neutrophil phagocytic activity that is not inhibited by pepsin digestion (Miyauchi et al., 1998).

The data indicates an effect of treatment with CDFA that was associated with the route of administration. While the subcutaneous route was associated with a greater median fluorescence intensity per macrophage, oral administration was associated with a greater PMN MFI. However, regardless of the route of administration, treatment was associated with a significant increase in the PMN HPC/LPC percent ratio. This finding was demonstrated in Experiments IV and V. In addition, dose-related responses were demonstrated in animals treated by intra-gastric tubing (Experiment V).

The foregoing description and figures comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and figures merely explain and illustrate the invention, and the invention is not limited thereto, except insofar as the claims are so limited. Those skilled in the art who have the disclosure before them will be able to make modifications and variations therein without departing from the scope of the invention.

I claim:

1. A method for enhancing immune responses in human and animal recipients comprising administering a spray-dried preparation of pasteurized and homogenized first milking colostrum wherein said preparation is formulated in a dosage amount between about 6 and about 12 grams; said administration comprising administering orally at a concentration which enhances immune response and at a conditioning dosage between about 6 and about 12 grams administered once per day during a conditioning period of time from about 7 to 14 days; and at a maintenance dose of about 6 grams administered once per day during a period following the conditioning period.

2. The method of claim 1 wherein administration enhances the immune response in a recipient in a dose-dependent manner.

3. The method of claim 1 wherein administration enhances the immune response in a recipient by increasing expression of CD11b positive receptors on blood lymphocytes.

4. The method of claim 1 wherein administration enhances immune response in a recipient by increasing CD11b receptor density on blood lymphocytes.

5. The method of claim 1 wherein administration enhances immune response in a recipient by increasing expression of CD4 positive receptors on lymphocytes.

6. The method of claim 1 wherein administration enhances immune response in a recipient by enhancing leukocyte activation.

7. The method of claim 1 wherein administration enhances immune response in a recipient by increasing phagocytic function in macrophage cells.

8. The method of claim 1 wherein administration enhances immune response in a recipient by increasing phagocytic function in polymorphonuclear (PMN) cells.

9. The method of claim 1 wherein administration enhances immune response in a recipient by increasing expression of activated PMN cells.

10. The method of claim 1 wherein administration enhances immune response in a recipient by increasing expression of CD11b positive PMN cells.

* * * * *